(12) United States Patent
Allawi et al.

(10) Patent No.: US 11,345,949 B2
(45) Date of Patent: May 31, 2022

(54) METHYLATED CONTROL DNA

(71) Applicant: Exact Sciences Corporation, Madison, WI (US)

(72) Inventors: Hatim T. Allawi, Middleton, WI (US); Graham P. Lidgard, Middleton, WI (US)

(73) Assignee: Exact Sciences Corporation, Madison, WI (US)

( * ) Notice: Subject to any disclaimer, the term of this patent is extended or adjusted under 35 U.S.C. 154(b) by 372 days.

(21) Appl. No.: 16/318,580

(22) PCT Filed: Jul. 19, 2017

(86) PCT No.: PCT/US2017/042902
§ 371 (c)(1),
(2) Date: Jan. 17, 2019

(87) PCT Pub. No.: WO2018/017740
PCT Pub. Date: Jan. 25, 2018

(65) Prior Publication Data
US 2019/0218601 A1    Jul. 18, 2019

Related U.S. Application Data

(60) Provisional application No. 62/364,082, filed on Jul. 19, 2016.

(51) Int. Cl.
*C12Q 1/68* (2018.01)
*C12Q 1/6827* (2018.01)

(52) U.S. Cl.
CPC ..... *C12Q 1/6827* (2013.01); *C12Q 2523/125* (2013.01); *C12Q 2531/113* (2013.01); *C12Q 2545/101* (2013.01); *C12Q 2561/109* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,011,769 A | 4/1991 | Duck et al. | |

(Continued)

FOREIGN PATENT DOCUMENTS

| | | |
|---|---|---|
| WO | WO 1995/00669 | 1/1995 |
| WO | WO 1995/15373 | 6/1995 |

(Continued)

OTHER PUBLICATIONS

Didenko, DNA Probes Using Fluorescence Resonance Energy Transfer, Biotechniques (2001) 31(5); 1106-1121. (Year: 2001).*

(Continued)

*Primary Examiner* — Jeanine A Goldberg
*Assistant Examiner* — Jennifer L. Overly
(74) *Attorney, Agent, or Firm* — Casimir Jones, S.C.; Mary Ann D. Brow

(57) ABSTRACT

Provided herein is technology relating compositions and methods for analysis of methylated DNA from a subject. The technology also relates to use of endogenous methylated DNAs as internal controls for marker gene methylation assays.

10 Claims, 7 Drawing Sheets

Specification includes a Sequence Listing.

B3GALT6 (hg19_dna range=chr1: 1163595-1163733 strand=+ )

Untreated Target (UT) Target Sequence

```
5'GGCCACACAGGCCCACTCTGGCCCTCTGAGCCCCGGCGGACCCAGGGCATTCAAGGAGCGGCTCTGGGCTGCCAGCGCAGGCCTCC
GCGCAAACACAGCAGGCTGGAAGTGGCGCTCATCACCGGCACGTCTTCCCAG 3'      (SEQ ID NO:1)
```

Bisulfite-treated (BT) Target Sequence

```
5'GGTTATATAGGTTTATTTTGGTTTTTTGAGTTTTCGGCGGATTTAGGGTATTTAAGGAGCGGTTTTGGGTTGTTAGCGTAGGTTTTC
GCGTAAATATAGTAGGTTGGAAGTGGCGTTTATTATCGGTACGTTTTTTAG 3'       (SEQ ID NO:2)
```

QuARTS flap endonuclease assay oligonucleotides:

| | | |
|---|---|---|
| B3GALT6 forward primer | 5'GGTTTATTTTGGTTTTTTGAGTTTTCGG 3' | (SEQ ID NO:3) |
| B3GALT6 reverse primer | 5'TCCAACCTACTATATTTACGCGAA 3' | (SEQ ID NO:4) |
| B3GALT6 Probe (arm 3) | 5'GACGCGGAGGCGGATTTAGGG/3C6/ 3' | (SEQ ID NO:5) |
| B3GALT6 Probe (arm 5) | 5'CCACGGACGGCGGATTTAGGG/3C6/ 3' | (SEQ ID NO:6) |

(56) References Cited

U.S. PATENT DOCUMENTS

| | | |
|---|---|---|
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,494,810 A | 2/1996 | Barany et al. |
| 5,624,802 A | 4/1997 | Urdea et al. |
| 5,639,611 A | 6/1997 | Wallace et al. |
| 5,660,988 A | 8/1997 | Duck et al. |
| 5,670,325 A | 9/1997 | Lapidus et al. |
| 5,710,264 A | 1/1998 | Urdea et al. |
| 5,741,650 A | 4/1998 | Lapidus et al. |
| 5,773,258 A | 6/1998 | Birch et al. |
| 5,786,146 A | 7/1998 | Herman et al. |
| 5,792,614 A | 8/1998 | Western et al. |
| 5,830,665 A | 11/1998 | Shuber et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,888,778 A | 3/1999 | Shuber |
| 5,914,230 A | 6/1999 | Liu et al. |
| 5,928,870 A | 7/1999 | Lapidus et al. |
| 5,952,178 A | 9/1999 | Lapidus et al. |
| 5,958,692 A | 9/1999 | Cotton et al. |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,020,137 A | 2/2000 | Lapidus et al. |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,143,529 A | 11/2000 | Lapidus et al. |
| 6,146,828 A | 11/2000 | Lapidus et al. |
| 6,150,097 A | 11/2000 | Tyagi et al. |
| 6,183,960 B1 | 2/2001 | Lizardi |
| 6,203,993 B1 | 3/2001 | Shuber et al. |
| 6,210,884 B1 | 4/2001 | Lizardi |
| 6,221,583 B1 | 4/2001 | Kayyem et al. |
| 6,235,502 B1 | 5/2001 | Weissman et al. |
| 6,248,229 B1 | 6/2001 | Meade |
| 6,251,594 B1 | 6/2001 | Gonzalgo et al. |
| 6,265,171 B1 | 7/2001 | Herman et al. |
| 6,268,136 B1 | 7/2001 | Shuber et al. |
| 6,280,947 B1 | 8/2001 | Shuber et al. |
| 6,300,077 B1 | 10/2001 | Shuber et al. |
| 6,303,304 B1 | 10/2001 | Shuber et al. |
| 6,351,857 B2 | 3/2002 | Slaon, III et al. |
| 6,406,857 B1 | 6/2002 | Shuber et al. |
| 6,415,455 B1 | 7/2002 | Slaon, III et al. |
| 6,428,964 B1 | 8/2002 | Shuber |
| 6,475,738 B2 | 11/2002 | Shuber et al. |
| 6,482,595 B2 | 11/2002 | Shuber et al. |
| 6,498,012 B2 | 12/2002 | Laken |
| 6,503,718 B2 | 1/2003 | Shuber et al. |
| 6,586,177 B1 | 1/2003 | Shuber |
| 6,551,777 B1 | 4/2003 | Shuber et al. |
| 6,750,020 B2 | 6/2004 | Shuber |
| 6,818,404 B2 | 11/2004 | Shuber |
| 6,844,155 B2 | 1/2005 | Shuber |
| 6,849,403 B1 | 2/2005 | Shuber |
| 6,872,816 B1 | 3/2005 | Hall et al. |
| 6,919,174 B1 | 7/2005 | Shuber |
| 6,964,846 B1 | 11/2005 | Shuber |
| 7,368,233 B2 | 5/2008 | Shuber et al. |
| 7,662,594 B2 | 2/2010 | Kong et al. |
| 7,981,612 B2 | 7/2011 | Shuber et al. |
| 8,361,720 B2 | 1/2013 | Oldham-Haltom et al. |
| 8,715,937 B2 | 5/2014 | Zou et al. |
| 8,808,990 B2 | 8/2014 | Lidgard et al. |
| 8,916,344 B2 | 12/2014 | Zou et al. |
| 9,000,146 B2 | 4/2015 | Bruinsma et al. |
| 9,127,318 B2 | 9/2015 | Oldham-Haltom et al. |
| 9,163,278 B2 | 10/2015 | Bruinsma et al. |
| 9,169,511 B2 | 10/2015 | Lidgard et al. |
| 9,212,392 B2 | 12/2015 | Allawi et al. |
| 9,631,228 B2 | 4/2017 | Bruinsma et al. |
| 9,845,491 B2 | 12/2017 | Bruinsma et al. |
| 10,011,878 B2 | 7/2018 | Ahlquist et al. |
| 10,047,390 B2 | 8/2018 | Bruinsma et al. |
| 10,106,844 B2 | 10/2018 | Allawi et al. |
| 10,196,676 B2 | 2/2019 | Bruinsma et al. |
| 10,385,406 B2 | 8/2019 | Allawi et al. |
| 2007/0202525 A1 | 8/2007 | Quake et al. |
| 2009/0253142 A1 | 10/2009 | Allawi et al. |
| 2012/0262260 A1 | 10/2012 | Light et al. |
| 2012/0288868 A1 | 11/2012 | Bruinsma et al. |
| 2013/0022974 A1* | 1/2013 | Chinnaiyan .......... C12Q 1/6886 435/6.11 |
| 2014/0228231 A1 | 8/2014 | Vilain et al. |
| 2016/0168643 A1 | 6/2016 | Ahlquist et al. |
| 2016/0194721 A1 | 7/2016 | Allawi et al. |
| 2018/0245157 A1 | 8/2018 | Allawi et al. |
| 2018/0291469 A1 | 10/2018 | Ahlquist et al. |
| 2019/0153510 A1 | 5/2019 | Allawi et al. |
| 2019/0330702 A1 | 10/2019 | Allawi et al. |
| 2020/0040377 A1 | 2/2020 | Allawi et al. |

FOREIGN PATENT DOCUMENTS

| | | | |
|---|---|---|---|
| WO | WO 1997/46705 | 12/1997 | |
| WO | WO 1999/28498 | 6/1998 | |
| WO | WO 2000/26401 | 5/2000 | |
| WO | WO 2002/070755 | 9/2002 | |
| WO | WO 2005/023091 | 3/2005 | |
| WO | WO 2005/038051 | 4/2005 | |
| WO | WO 2007/039234 | 4/2007 | |
| WO | WO 2008/073303 | 6/2008 | |
| WO | WO 2012/155072 | 11/2012 | |
| WO | WO 2013/116375 | 8/2013 | |
| WO | WO 2014/036314 | 3/2014 | |
| WO | WO 2016/094839 | 6/2016 | |
| WO | WO 2017/192221 | * 11/2017 | ............... C12Q 1/68 |
| WO | WO 2017192221 | * 11/2017 | ............... C12Q 1/68 |
| WO | WO 2018/017710 | 1/2018 | |
| WO | WO 2018/140781 | 8/2018 | |

OTHER PUBLICATIONS

Illumina Product Guide (Year: 2010).*

Hernandez, Distinct DNA methylation changes highly correlated with chronological age in the human brain, Human Molecular Genetics (2011), vol. 20, No. 6, 1164-1172. (Year: 2011).*

Bai etal Biosynthesis of the Linkage Region of Glycosaminoglycans (2001) J Biological Chem (2001) 276:51,48189-48195 (Year: 2001).*

Ballabio, et al., Screening for steroid sulfatase (STS) gene deletions by multiplex DNA amplification, Human Genetics, 1990, 84(6): 571-573.

Barany, Genetic disease detection and DNA amplification using cloned thermostable ligase, Proc. Natl. Acad. Sci USA, 1991, 88:189-93.

Bustin, Absolute quantification of mRNA using real-time reverse transcription polymerase chain reaction assays, J. Molecular Endocrinology, 2000, 25:169-193.

Ceska et al., Structure-specific DNA cleavage by 5' nucleases. Trends Biochem Sci. Sep. 1998;23(9):331-6.

Chamberlain et al., Deletion screening of the Duchenne muscular dystrophy locus via multiplex DNA amplification, Nucleic Acids Research, 1988, 16(23):11141-11156.

Don et al., 'Touchdown' PCR to circumvent spurious priming during gene amplification, Nucleic Acids Research, 1991, 19(14):4008.

Eads et al., CpG island hypermethylation in human colorectal tumors is not associated with DNA methyltransferase overexpression. Cancer Res. May 1, 19995;59(10):2302-6.

Feil et al., Methylation analysis on individual chromosomes: improved protocol for bisulphite genomic sequencing. Nucleic Acids Res. Feb. 2, 19945;22(4):695-6.

(56) References Cited

OTHER PUBLICATIONS

Frommer et al., A genomic sequencing protocol that yields a positive display of 5-methylcytosine residues in individual DNA strands. Proc Natl Acad Sci USA. Mar. 1, 1992;89(5):1827-31.
Gonzalgo et al., Identification and characterization of differentially methylated regions of genomic DNA by methylation-sensitive arbitrarily primed PCR. Cancer Res. Feb. 1, 19975;57(4):594-9.
Gonzalgo et al., Rapid quantitation of methylation differences at specific sites using methylation-sensitive single nucleotide primer extension (Ms-SNuPE). Nucleic Acids Res. Jun. 1, 19975;25(12):2529-31.
Grafstrom RH, et al., The characteristics of DNA methylation in an in vitro DNA synthesizing system from mouse fibroblasts. Nucleic Acids Res. 1985;13(8): 2827-2842.
Grigg et al., Sequencing 5-methylcytosine residues in genomic DNA. Bioessays. Jun. 1994;16(6):431-6.
Grigg, Sequencing 5-methylcytosine residues by the bisulphite method. DNA Seq. 1996;6(4):189-98.
Gu et al., Genome-scale DNA methylation mapping of clinical samples at singlenucleotide resolution. Nat Methods. Feb. 2010;7(2):133-6.
Guilfoyle et al., Ligation-mediated PCR amplification of specific fragments from a class-II restriction endonuclease total digest, Nucleic Acids Research, 1997, 25:1854-1858.
Hall et al., Sensitive detection of DNA polymorphisms by the serial invasive signal amplification reaction, PNAS, 2000, 97:8272.
Hayden et al., Multiplex-Ready PCR: A new method for multiplexed SSR and SNP genotyping, BMC Genomics, 2008, 9:80.
Hecker et al., High and low annealing temperatures increase both specificity and yield in touchdown and stepdown PCR, Biotechniques, 1996, 20(3):478-485.
Herman et al., Methylation-specific PCR: a novel PCR assay for methylation status of CpG islands. Proc Natl Acad Sci USA 1996; 93: 9821-9826.
Higuchi et al., A general method of in vitro preparation and specific mutagenesis of DNA fragments: study of protein and DNA interactions, Nucleic Acids Research, 1988, 16(15):7351-7367.
Higuchi et al., Simultaneous amplification and detection of specific DNA sequences, Biotechnology, 1992, 10:413-417.
Higuchi et al.,Kinetic PCR analysis: real-time monitoring of DNA amplification reactions, Biotechnology, 1993, 11:1026-1030.
Kaiser et al., A comparison of eubacterial and archaeal structure-specific 5'-exonucleases. J Biol Chern. Jul. 2, 19993;274(30):21387-94.
Kalinina et al., Nanoliter scale PCR with TaqMan detection, Nucleic Acids Research, 1997, 25:1999-2004.
Laird, Principles and challenges of genome-wide DNA methylation analysis, Nat Rev Genet, 2010, 11: 191-203.
Liu et al., Flap endonuclease 1: a central component of DNA metabolism. Annu Rev Biochem. 2004;73:589-615.
Lyamichev et al.,Polymorphism identification and quantitative detection of genomic DNA by invasive cleavage of oligonucleotide probes, Nat. Biotech., 1999, 17:292-296.
Martin et al., Genomic sequencing indicates a correlation between DNA hypomethylation in the 5' region of the pS2 gene and its expression in human breast cancer cell lines. Gene. May 1, 19959;157(1-2):261-4.
Meissner et al., Reduced representation bisulfite sequencing for comparative high-resolution DNA methylation analysis. Nucleic Acids Res. Oct. 1, 20053;33(18):5868-77.
Nyce et al., Variable effects of DNA-synthesis inhibitors upon DNA methylation in mammalian cells. Nucleic Acids Res. May 2, 19867;14(10):4353-67.
Olek et al., A modified and improved method for bisulphite based cytosine methylation analysis. Nucleic Acids Res. Dec. 1, 19965;24(24):5064-6.
Olek et al., The pre-implantation ontogeny of the H19 methylation imprint. Nat Genet. Nov. 1997;17(3):275-6.
Olivier, The Invader assay for SNP genotyping, Mutat Res. Jun. 3, 2005;573(1-2):103-10.
Orpana, Fluorescence resonance energy transfer (FRET) using ssDNA binding fluorescent dye, Biomol Eng. Apr. 2004;21(2):45-50.
Ramsahoye et al., Non-CpG methylation is prevalent in embryonic stem cells and may be mediated by DNA methyltransferase 3a. Proc. Natl. Acad. Sci. USA, 2000; 97(10): 5237-5242.
Rein et al., Identifying 5-methylcytosine and related modifications in DNA genomes. Nucleic Acids Res. May 15, 1998;26(10):2255-64.
Roux, Using mismatched primer-template pairs in touchdown PCR, Biotechniques, 1994, 16(5):812-814.
Sadri et al., Rapid analysis of DNA methylation using new restriction enzyme sites created by bisulfite modification. Nucleic Acids Res. Dec. 15, 1996;24(24):5058-9.
Salomon R. et al., Methylation of Mouse DNA In Vivo: DI- and Tripyrimidine Sequences Containing 5-Methylcytosine. Biochim. Biophys. Acta. 1970;204: 340-351.
Schouten et al., Relative quantification of 40 nucleic acid sequences by multiplex ligation-dependent probe amplification, Nucleic Acids Research, 2002, 30(12): e57.
Selvin, Fluorescence resonance energy transfer, 1995, Methods Enzymol. 1995;246:300-34.
Stryer, Fluorescence energy transfer as a spectroscopic ruler, Annu Rev Biochem. 1978;47:819-46.
Toyota et al., Identification of differentially methylated sequences in colorectal cancer by methylated CpG island amplification. Cancer Res. May 15, 1999;59(10):2307-12.
Triglia et al., A procedure for in vitro amplification of DNA segments that lie outside the boundaries of known sequences, Nucleic Acids Res., 1988,16:8186.
Vogelstein et al. Digital PCR. Proc Natl Acad Sci USA. 1999;96; 9236-41.
Woodcock et al., The majority of methylated deoxycytidines in human DNA are not in the CpG dinucleotide. Biochem Biophys Res Commun. Jun. 15, 1987;145(2):888-94.
Xiong et al., COBRA: a sensitive and quantitative DNA methylation assay. Nucleic Acids Res. Jun. 15, 1997;25(12):2532-4.
Zeschnigk et al., Imprinted segments in the human genome: different DNA methylation patterns in the Prader-Willi/Angelman syndrome region as determined by the genomic sequencing method. Hum Mol Genet. Mar. 1997;6(3):387-95.
Zou et al., Highly methylated genes in colorectal neoplasia: implications for screening. Cancer Epidemiol Biomarkers Prev. Dec. 2007;16(12):2686-96.
Zou et al., Sensitive quantification of methylated markers with a novel methylation specific technology. Abstract D-144, Clin Chem 2010;56(6)Suppl:A199.
International Search Report and Written Opininon for PCT/US2017/042902, dated Nov. 27, 2017, 13 pages.
Extended European Search Report for EP 17831807.7, dated Dec. 20, 2019, 7 pages.

\* cited by examiner

FIG. 1

_B3GALT6_ (hg19_dna range=chr1: 1163595-1163733 strand=+)

Untreated Target (UT) Target Sequence

5' GGCCACACAGGCCCACTCTGGCCTCTGAGCCCCGGCGGACCCAGGGCATTCAAGGAGCGGCTCTGGGCTGCCAGCGCAGGCCTCC
GCGCAAACACAGGCTGGAAGTGGCGCTCATCACCGGCACGTCTTCCCAG 3'        (SEQ ID NO:1)

Bisulfite-treated (BT) Target Sequence

5' GGTTATATAGGTTTATTTTGGTTTTTCGGCGGATTTAGGGTATTTAAGGAGCGGTTTTGGGTTGTTAGCGTAGGTTTTC
GCGTAAATATAGTAGGTTGGAAGTGGCGTTTATTATCGGTACGTTTTTTAG 3'       (SEQ ID NO:2)

QuARTS flap endonuclease assay oligonucleotides:

| | | |
|---|---|---|
| B3GALT6 forward primer | 5' GGTTTATTTGGTTTTTTGAGTTTTCGG 3' | (SEQ ID NO:3) |
| B3GALT6 reverse primer | 5' TCCAACCTACTATATTTACGCGAA 3' | (SEQ ID NO:4) |
| B3GALT6 Probe (arm 3) | 5' GACGCGGAGGCGGATTTAGG/3C6/ 3' | (SEQ ID NO:5) |
| B3GALT6 Probe (arm 5) | 5' CCACGGACGGCGGATTTAGGG/3C6/ 3' | (SEQ ID NO:6) |

FIG. 2

*β-actin Target DNAs*

Untreated Target (UT) Sequence

5'CTCTGACCTGAGTCTCCTTGGAACTCTGCAGGTTCTATTTGCTTTTTCCCAGATGAGCTCTTTTTCTGGTGTTGTCTCTGACT
AGGTGTCTAAGACAGTGTTGTGGGTAGTACTAACACTGGCTCGTGTGACAAGGCCATGAGGCTGGTGTAAAGCGGCCTTGGAGTGT
GTATTAAGTAGGTGCACAGTAGGTCTGAACAGAGACTCCCCATCCCCAAGA3' (SEQ ID NO:7)

Bisulfite-treated (BT) Target Sequence

5'TTTTGATTTGAGTTTTTTTTTGGAATTTTGTAGGTTTTATTTGTTTTTTTTAGATGAGTTTTTTTTTGGTGTTGTTTTTGATT
AGGTGTTTAAGATAGTGTTGTGGGTAGTATTAATATGGTTTGTGTGATAAGGTTATGAGGTTGTGTAAAGTGGTTTGGAGTGT
GTATTAAGTAGGTGTATAGTAGGTTTGAATAGATTTTTATTTAAGA3' (SEQ ID NO:8)

QuARTS flap endonuclease assay oligonucleotides:

For bisulfite-converted target DNA
β-actin BT forward primer:    5' GTGTTTGTTTTTTGATTAGGTGTTTAAGA 3'    (SEQ ID NO:9)
β-actin BT reverse primer:    5' CTTTACACCAACCTCATAACCTTATC 3'        (SEQ ID NO:10)
β-actin BT probe (Arm 3):     5' GACGCGGAGATAGTGTTGTGG/3C6/ 3'        (SEQ ID NO:11)

FRET cassette oligonucleotides:

Arm 3 QUASAR-670    5'Q670/TCT/BHQ_2/AGCCGGTTTTCCGGCTGAGACTCCGCGTC/3C6    (SEQ ID NO:12)
Arm 5 FAM           5'd-FAM-TCT-BHQ-1-AGCCGGTTTTCCGGCTGAGACGTCCGTGG-C6    (SEQ ID NO:13)

SEQUENCE LISTING

<160> NUMBER OF SEQ ID NOS: 13

<210> SEQ ID NO 1
<211> LENGTH: 139
<212> TYPE: DNA
<213> ORGANISM: Homo sapiens

<400> SEQUENCE: 1
ggccacacag gcccactctg gccctctgag cccccggcgg acccagggca ttcaaggagc    60
ggctctgggc tgccagcgca ggcctccgcg caaacacagc aggctggaag tggcgctcat   120
caccggcacg tcttcccag                                                139

<210> SEQ ID NO 2
<211> LENGTH: 139
<212> TYPE: DNA
<213> ORGANISM: Homo sapiens

<400> SEQUENCE: 2
ggttatatag gtttattttg gttttttgag ttttcggcgg atttagggta tttaaggagc    60
ggttttgggt tgttagcgta ggttttcgcg taaatatagt aggttggaag tggcgtttat   120
tatcggtacg tttttttag                                                139

<210> SEQ ID NO 3
<211> LENGTH: 28
<212> TYPE: DNA
<213> ORGANISM: ArtIficial sequence
<220> FEATURE:
<223> OTHER INFORMATION: Synthetic

<400> SEQUENCE: 3
ggtttatttt ggtttttga gttttcgg                                       28

<210> SEQ ID NO 4
<211> LENGTH: 24
<212> TYPE: DNA
<213> ORGANISM: Artificial sequence
<220> FEATURE:
<223> OTHER INFORMATION: Synthetic

<400> SEQUENCE: 4
tccaacctac tatatttacg cgaa                                          24

<210> SEQ ID NO 5

```
<211> LENGTH: 21
<212> TYPE: DNA
<213> ORGANISM: Artificial sequence
<220> FEATURE:
<223> OTHER INFORMATION: Synthetic

<400> SEQUENCE: 5
gacgcggagg cggatttagg g                                                   21

<210> SEQ ID NO 6
<211> LENGTH: 21
<212> TYPE: DNA
<213> ORGANISM: Artificial sequence
<220> FEATURE:
<223> OTHER INFORMATION: Synthetic

<400> SEQUENCE: 6
ccacggacgg cggatttagg g                                                   21

<210> SEQ ID NO 7
<211> LENGTH: 224
<212> TYPE: DNA
<213> ORGANISM: Homo sapiens

<400> SEQUENCE: 7
ctctgacctg agtctccttt ggaactctgc aggttctatt tgcttttcc cagatgagct          60 cttttctgg tgtttgtctc tctgactagg tgtctaagac agtgttgtgg gtgtaggtac         120
taacactggc tcgtgtgaca aggccatgag gctggtgtaa agcggccttg gagtgtgtat        180
taagtaggtg cacagtaggt ctgaacagac tccccatccc aaga                         224

<210> SEQ ID NO 8
<211> LENGTH: 224
<212> TYPE: DNA
<213> ORGANISM: Homo sapiens

<400> SEQUENCE: 8
ttttgatttg agttttttt ggatttttgt aggttttatt tgttttttt tagatgagtt           60 ttttttttgg tgtttgtttt tttgattagg tgtttaagat agtgttgtgg gtgtaggtat        120
taatattggt ttgtgtgata aggttatgag gttggtgtaa agtggttttg gagtgtgtat        180
taagtaggtg tatagtaggt ttgaatagat tttttatttt aaga                         224

<210> SEQ ID NO 9
<211> LENGTH: 30
<212> TYPE: DNA
<213> ORGANISM: Artificial sequence
<220> FEATURE:
<223> OTHER INFORMATION: Synthetic

<400> SEQUENCE: 9
gtgtttgttt ttttgattag gtgtttaaga                                          30

<210> SEQ ID NO 10
<211> LENGTH: 26
<212> TYPE: DNA
<213> ORGANISM: Artificial sequence
<220> FEATURE:
<223> OTHER INFORMATION: Synthetic

<400> SEQUENCE: 10
ctttacacca acctcataac cttatc                                              26
```

```
<210> SEQ ID NO 11
<211> LENGTH: 21
<212> TYPE: DNA
<213> ORGANISM: Artificial sequence
<220> FEATURE:
<223> OTHER INFORMATION: Synthetic

<400> SEQUENCE: 11
gacgcggaga tagtgttgtg g                                              21

<210> SEQ ID NO 12
<211> LENGTH: 29
<212> TYPE: DNA
<213> ORGANISM: Artificial sequence
<220> FEATURE:
<223> OTHER INFORMATION: Synthetic

<400> SEQUENCE: 12
agccggtttt ccggctgaga ctccgcgtc                                      29

<210> SEQ ID NO 13
<211> LENGTH: 29
<212> TYPE: DNA
<213> ORGANISM: Artificial sequence
<220> FEATURE:
<223> OTHER INFORMATION: Synthetic

<400> SEQUENCE: 13
agccggtttt ccggctgaga cgtccgtgg                                      29
```

METHYLATED CONTROL DNA

CROSS-REFERENCE TO RELATED APPLICATIONS

The present application claims the priority benefit of U.S. Provisional Patent Application 62/364,082, filed Jul. 19, 2016, which is incorporated by reference in its entirety.

FIELD OF INVENTION

Provided herein is technology relating compositions and methods for analyzing and quantifying DNA, e.g., methylated DNA, in a subject. The technology relates to use of a methylated reference marker as an internal control in methylation assays in samples such as blood, plasma, stool, or tissue samples from a subject.

BACKGROUND

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) "Principles and challenges of genome-wide DNA methylation analysis" *Nat Rev Genet* 11: 191-203). Furthermore, in other cancers like sporadic colon cancer, methylation markers offer excellent specificity and are more broadly informative and sensitive than are individual DNA mutations (Zou et al (2007) "Highly methylated genes in colorectal neoplasia: implications for screening" *Cancer Epidemiol Biomarkers Prev* 16: 2686-96).

Nucleic acids from patient samples, e.g., blood, stool, and tissue samples, that are analyzed for the presence of mutations and/or for methylation status associated with disease or risk of disease typically pass through a number of process steps during analysis. These steps may comprise, e.g., filtration, precipitation, capture, washing, elution, and/or chemical modification. For analysis of DNAs to determine methylation status, e.g., the percent methylation of a test DNA, processing typically comprises treatment with bisulfite to convert un-methylated dC bases to dU residues, making them more readily distinguishable from the methyl-C residues that are protected from bisulfite conversion.

Accurate quantitation of a test DNA (e.g., determining percent methylation, presence and amount of DNA carrying a mutation, etc.) typically requires normalization to a control nucleic acid, e.g., an endogenous invariant gene having known features (e.g., known sequence, known copy-number per cell). Normalizing controls for sample-to-sample variations that may occur in, for example, sample processing, assay efficiency, etc., and allows accurate sample-to-sample data comparison.

SUMMARY

Provided herein is technology relating to characterizing samples, e.g., blood samples, stool samples, etc., for the presence or absence of, and/or the amounts of different species of nucleic acids that, for example, may be associated with a health status of a subject. The technology relates to methylated control DNA that can be processed and detected alongside methylated marker DNA indicative of disease. In some embodiments the technology provides composition comprising a B3GALT6 nucleic acid. For example, in some embodiments, a composition comprising a complex of a bisulfite-converted B3GALT6 nucleic acid and at least one oligonucleotide, wherein at least a portion of said oligonucleotide is hybridized to said B3GALT6 nucleic acid, is provided. In preferred embodiments, the B3GALT6 nucleic acid is a strand of DNA comprising the nucleotide sequence of SEQ ID NO:2 or the complement thereof. The oligonucleotide is not limited to any particular type of oligonucleotide, and may comprise, e.g., DNA, RNA, and/or PNA (peptide nucleic acid). In some embodiments, the oligonucleotide is a primer oligonucleotide.

In some embodiments the composition further comprises a detection probe oligonucleotide, the detection probe oligonucleotide comprising a region that is complementary to a portion of a strand of B3GALT6 DNA. In certain preferred embodiments, the detection probe oligonucleotide comprises a region that is complementary to a portion of SEQ ID NO:2 or the complement thereof.

The detection probe is not limited to any particular configuration and, e.g., may be a detection probe for use in PCR, LCR, invasive cleavage assays, QuARTS flap assays, and/or any nucleic acid detection assay known to those of skill in the art, examples of which are described hereinbelow. In some embodiments a detection probe oligonucleotide comprises a reporter molecule, e.g., a reactive moiety or a fluorophore. In some embodiments the detection probe oligonucleotide comprises a flap sequence.

The composition comprising the B3GALT6 nucleic acid and the oligonucleotide may comprise other components. For example, in some embodiments the composition further comprises a FRET cassette, a FEN-1 endonuclease, and/or a thermostable DNA polymerase. In some embodiments, the compositions described above are present together in a reaction mixture, e.g., for a nucleic acid detection assay. In some embodiments the reaction mixture further comprises one or more of a primer, flap oligonucleotide, a thermostable DNA polymerase, a FEN-1 endonuclease, and/or a FRET cassette.

In some embodiments, the technology provides a kit comprising B3GALT6-related nucleic acid. For example, in some embodiments the technology provides a kit comprising a) at least one oligonucleotide, wherein at least a portion of the oligonucleotide specifically hybridizes to bisulfite-converted B3GALT6 DNA; and b) bisulfite reagent. In some preferred embodiments, the at least one oligonucleotide comprises a region that is complementary to a portion of SEQ ID NO:2 or a complement thereof. By way of example and not of limitation, in some embodiments, the oligonucleotide is selected from one or more of a capture oligonucleotide, a pair of nucleic acid primers, a nucleic acid probe, and an invasive oligonucleotide. In some embodiments the kit further comprises a synthetic methylated DNA that has essentially no homology to mammalian DNA for use, e.g., as a run control. In preferred embodiments, the synthetic methylated DNA is a zebrafish DNA, e.g., a synthetic portion of the zebrafish rassf1 gene, as described in U.S. Provisional Patent Appl. Ser. No. 62/364,049.

The technology further provides methods of characterizing samples. In some embodiments, the method comprises a) treating DNA from a sample with a bisulfite reagent to produce bisulfite-converted DNA, and b) amplifying a region of the bisulfite-converted DNA using a pair of nucleic acid primers, wherein the amplifying produces amplified product having a sequence comprising a region of SEQ ID NO:2. In some preferred embodiments, the amplified product has a sequence comprising the entirety of SEQ ID NO:2.

In embodiments the method further comprises a step of detecting the amplified product with a detection probe. As discussed above, the detection probe is not limited to any particular form or function of detection probe. In some embodiments the detection probe comprises a reporter molecule, which in some embodiments the detection probe comprises a flap sequence.

BRIEF DESCRIPTION OF THE DRAWINGS

These and other features, aspects, and advantages of the present technology will become better understood with regard to the following drawings:

FIG. 1 shows a schematic diagram of a B3GALT6 (hg19_dna range=chr1: 1163595-1163733 strand=+) marker target region in unconverted form and bisulfite-treated form. Flap assay primers and probes for detection of bisulfate-converted B3GALT6 DNA are shown.

FIG. 2 shows a schematic diagram of a β-actin target region in unconverted form and bisulfate-treated form. Flap assay primers and probes for detection of bisulfate-converted β-actin DNA are shown.

DEFINITIONS

Figure 3:
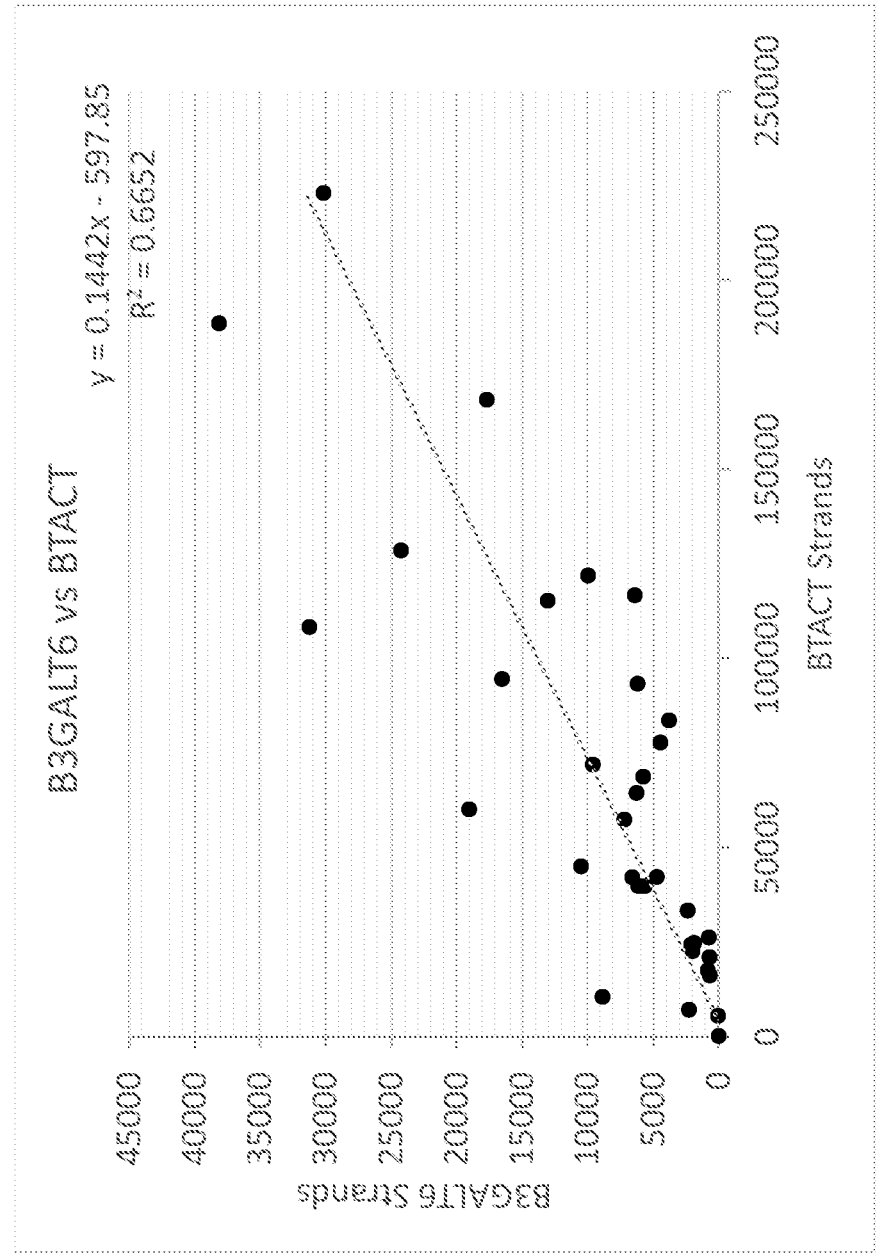
FIG. 3 provides a graph comparing the detection of bisulfate-converted B3GALT6 DNA to bisulfate-converted β-actin DNA in DNA extracted from 32 lung tissue samples, as described in Example 3.

To facilitate an understanding of the present technology, a number of terms and phrases are defined below. Additional definitions are set forth throughout the detailed description.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

As used herein, "a" or "an" or "the" can mean one or more than one. For example, "a" widget can mean one widget or a plurality of widgets.

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, the term "analyte" is to be construed broadly as any compound, molecule, element, ion, or other substance of interest to be detected, identified, or characterized.

As used herein, the terms "subject" and "patient" refer to any animal, such as a dog, cat, bird, livestock, and particularly a mammal, preferably a human. In some instances, the subject is also a "user" (and thus the user is also the subject or patient).

As used herein, the term "sample" and "specimen" are used interchangeably, and in the broadest senses. In one sense, sample is meant to include a specimen or culture obtained from any source, as well as biological and environmental samples. Biological samples may be obtained from animals (including humans) and encompass fluids, solids, tissues, and gases. Biological samples include blood products, such as plasma, serum, stool, urine, and the like. Environmental samples include environmental material such as surface matter, soil, mud, sludge, biofilms, water, crystals, and industrial samples. Such examples are not however to be construed as limiting the sample types applicable to the present invention.

As used herein, a "remote sample" as used in some contexts relates to a sample indirectly collected from a site that is not the cell, tissue, or organ source of the sample. For instance, when sample material originating from the pancreas is assessed in a stool sample (e.g., not from a sample taken directly from a pancreas), the sample is a remote sample.

The term "target," when used in reference to a nucleic acid capture, detection, or analysis method, generally refers to a nucleic acid having a feature, e.g., a particular sequence of nucleotides to be detected or analyzed, e.g., in a sample suspected of containing the target nucleic acid. In some embodiments, a target is a nucleic acid having a particular sequence for which it is desirable to determine a methylation status. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "segment" is defined as a region of nucleic acid within the target sequence. The term "sample template" refers to nucleic acid originating from a sample that is analyzed for the presence of a target.

The term "marker", as used herein, refers to a substance (e.g., a nucleic acid, or a region of a nucleic acid, or a protein) that may be used to distinguish non-normal cells (e.g., cancer cells) from normal cells, e.g., based on presence, absence, or status (e.g., methylation state) of the marker substance.

As used herein the term "fish DNA" is distinct from zebrafish DNA and refers to exogenous non-target DNA isolated from fish. The term "exogenous" as used in reference to non-target DNA refers to non-target DNA that is isolated and purified from a source other than the source or sample containing the target DNA. Such exogenous DNA is selected to be undetected by an assay configured to detect and/or quantify the target nucleic acid in the reaction to which the exogenous DNA is added. For example, purified fish DNA is exogenous DNA with respect to a sample comprising human target DNA, e.g., as described in U.S.

Pat. No. 9,212,392, which is incorporated herein by reference. Bulk purified fish DNA is commercially available, e.g., provided in the form of cod and/or herring sperm DNA (Roche Applied Science, Mannheim, Germany) or salmon DNA (USB/Affymetrix).

As used herein, the term "zebrafish DNA" is distinct from fish DNA and refers to DNA isolated from *Danio rerio*, or created in vitro (e.g., enzymatically; synthetically) to have a sequence of nucleotides found in DNA from *Danio rerio* as described, e.g., in U.S. Provisional Patent Appl. Ser. No. 62/364,049, filed Jul. 19, 2016, which is incorporated herein by reference in its entirety. In preferred embodiments, the zebrafish DNA is a methylated DNA added as a detectable control DNA, e.g., a process control for verifying DNA recovery through sample processing steps.

As used herein, the term "locus" refers to a particular position, e.g., of a mutation, polymorphism, or a C residue in a CpG dinucleotide, within a defined region or segment of nucleic acid, such as a gene or any other characterized sequence on a chromosome or RNA molecule. A locus is not limited to any particular size or length, and may refer to a portion of a chromosome, a gene, functional genetic element, or a single nucleotide or base pair. As used herein in reference to CpG sites that may be methylated, a locus refers to the C residue in the CpG dinucleotide.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO/05023091A2; US Patent Application Publication No. 20070202525; each of which is incorporated herein by reference in its entirety).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985, 557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in US Patent Publication US 20090253142 A1 (application Ser. No. 12/404,240), incorporated herein by reference in its entirety for all purposes. Additional amplification plus invasive cleavage detection configurations, termed the QuARTS method, are described in U.S. Pat. Nos. 8,361,720; 8,715,937; 8,916,344; and 9,127,318, incorporated herein by reference in their entireties for all purposes. The term "invasive cleavage structure" as used herein refers to a cleavage structure comprising i) a target nucleic acid, ii) an upstream nucleic acid (e.g., an invasive or "INVADER" oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain). As used herein, the term "flap endonuclease assay" includes "INVADER" invasive cleavage assays and QuARTS assays, as described above.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label. When used in reference to flap assay, the term refers to an oligonucleotide that interacts with a target nucleic acid to form a cleavage structure in the presence of an invasive oligonucleotide. As used in reference to a flap assay, the terms "flap probe" and "flap oligonucleotide" are used interchangeably.

The term "invasive oligonucleotide" refers to an oligonucleotide that hybridizes to a target nucleic acid at a location adjacent to the region of hybridization between a probe and the target nucleic acid, wherein the 3' end of the invasive oligonucleotide comprises a portion (e.g., a chemical moiety, or one or more nucleotides) that overlaps with the region of hybridization between the probe and target. The 3' terminal nucleotide of the invasive oligonucleotide may or may not base pair a nucleotide in the target. In some embodiments, the invasive oligonucleotide contains sequences at its 3' end that are substantially the same as sequences located at the 5' end of a portion of the probe oligonucleotide that anneals to the target strand.

The term "flap endonuclease" or "FEN," as used herein, refers to a class of nucleolytic enzymes, typically 5' nucleases, that act as structure-specific endonucleases on DNA structures with a duplex containing a single stranded 5' overhang, or flap, on one of the strands that is displaced by another strand of nucleic acid (e.g., such that there are overlapping nucleotides at the junction between the single and double-stranded DNA). FENs catalyze hydrolytic cleavage of the phosphodiester bond at the junction of single and double stranded DNA, releasing the overhang, or the flap. Flap endonucleases are reviewed by Ceska and Savers (Trends Biochem. Sci. 1998 23:331-336) and Liu et al (Annu. Rev. Biochem. 2004 73: 589-615; herein incorporated by reference in its entirety). FENs may be individual enzymes, multi-subunit enzymes, or may exist as an activity of another enzyme or protein complex (e.g., a DNA polymerase).

A flap endonuclease may be thermostable. For example, FEN-1 flap endonuclease from archaeal thermophilic organisms are typical thermostable. As used herein, the term "FEN-1" refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term "cleaved flap" refers to a single-stranded oligonucleotide that is a cleavage product of a flap assay.

The term "cassette," when used in reference to a flap cleavage reaction, refers to an oligonucleotide or combination of oligonucleotides configured to generate a detectable signal in response to cleavage of a flap or probe oligonucleotide, e.g., in a primary or first cleavage structure formed in a flap cleavage assay. In preferred embodiments, the cassette hybridizes to a non-target cleavage product produced by cleavage of a flap oligonucleotide to form a second overlapping cleavage structure, such that the cassette can then be cleaved by the same enzyme, e.g., a FEN-1 endonuclease.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label, e.g., a fluorophore. In particularly preferred embodiments, a cassette comprises labeled moieties that produce a FRET effect.

As used herein, the term "FRET" refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor fluorophore to a non-fluorescing molecule (e.g., a "dark" quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

In an exemplary flap detection assay, an invasive oligonucleotide and flap oligonucleotide are hybridized to a target nucleic acid to produce a first complex having an overlap as described above. An unpaired "flap" or "arm" is included on the 5' end of the flap oligonucleotide. The first complex is a substrate for a flap endonuclease, e.g., a FEN-1 endonuclease, which cleaves the flap oligonucleotide to release the 5' flap portion. In a secondary reaction, the released 5' flap product serves as an invasive oligonucleotide on a FRET cassette to again create the structure recognized by the flap endonuclease, such that the FRET cassette is cleaved. When the fluorophore and the quencher are separated by cleavage of the FRET cassette, a detectable fluorescent signal above background fluorescence is produced.

The term "real time" as used herein in refers to detection of nucleic acid amplification or signal amplification by the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR or QUARTS reactions is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the term "quantitative amplification data set" refers to the data obtained during quantitative amplification of the target sample, e.g., target DNA. In the case of quantitative PCR or QuARTS assays, the quantitative amplification data set is a collection of fluorescence values obtained during amplification, e.g., during a plurality of, or all of the thermal cycles. Data for quantitative amplification is not limited to data collected at any particular point in a reaction, and fluorescence may be measured at a discrete point in each cycle or continuously throughout each cycle.

The abbreviations "Ct" and "Cp" as used herein, in reference to data collected during real time PCR and PCR+ INVADER assays, refer to the cycle at which signal (e.g., fluorescent signal) crosses a predetermined threshold value indicative of positive signal. Various methods have been used to calculate the threshold that is used as a determinant of signal verses concentration, and the value is generally expressed as either the "crossing threshold" (Ct) or the "crossing point" (Cp). Either Cp values or Ct values may be used in embodiments of the methods presented herein for analysis of real-time signal for the determination of the percentage of variant and/or non-variant constituents in an assay or sample.

As used herein, the terms "complementary" or "complementarity" used in reference to polynucleotides (i.e., a sequence of nucleotides) refers to polynucleotides related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally, as in a purified restriction digest, or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like). The primer is typically single stranded for maximum efficiency in amplification, but may alternatively be partially or completely double stranded. The portion of the primer that hybridizes to a template nucleic acid is sufficiently long to prime the synthesis of extension products in the presence of the inducing agent. The exact lengths of the primers will depend on many factors, including temperature, source of primer and the use of the method. Primers may comprise labels, tags, capture moieties, etc.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "Process For Preparing Polynucleotides," issued Jul. 3, 1984 to Caruthers et al., or other methods known to those skilled in the art. All of these references are incorporated by reference.

A "sequence" of a biopolymer refers to the order and identity of monomer units (e.g., nucleotides, amino acids, etc.) in the biopolymer. The sequence (e.g., base sequence) of a nucleic acid is typically read in the 5' to 3' direction.

As used herein, the term "gene" refers to a nucleic acid (e.g., DNA) sequence that comprises coding sequences necessary for the production of a polypeptide, precursor, or RNA (e.g., non-coding RNAs such as ribosomal RNA, transfer RNA, splicosomal RNA, microRNA). A polypeptide or non-coding RNA can be encoded by a full length coding sequence or by any portion of the coding sequence so long as the desired activity or functional properties (e.g., enzymatic activity, ligand binding, signal transduction, immunogenicity, etc.) of the full-length or fragment polypeptide are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (e.g., hnRNA); introns may contain regulatory elements (e.g., enhancers). Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

The term "highly methylated" refers to nucleic acids in which a particular locus (e.g., a CpG dinucleotide or set of dinucleotides or CpG-rich region) is methylated in a particular sample type or tissue type at a rate that is measurably greater than is observed for the comparable locus in the same DNA in another tissue or sample type. "Highly methylated" may refer to a single particular C-residue or to an average rate of methylation across multiple Cs in a region, as a fraction of the copies of that locus in the sample being assayed. Without limiting the term to any particular level of methylation, in some embodiments, a highly methylated locus may be >10% methylated, preferably >20% to 40%, more preferably >50% to 75%, still more preferably between 75% and 100%.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g., Antequera et al. (1990) *Cell* 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) *J. Mol. Biol.* 196: 261-281. For example, the observed CpG frequency over expected frequency can be calculated according to the formula R=(A×B)/(C×D), where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) *Proc. Natl. Acad. Sci. USA* 97: 5237-5242; Salmon and Kaye (1970) *Biochim. Biophys. Acta.* 204: 340-351; Grafstrom (1985) *Nucleic Acids Res.* 13: 2827-2842; Nyce (1986) *Nucleic Acids Res.* 14: 4353-4367; Woodcock (1987) *Biochem. Biophys. Res. Commun.* 145: 888-894).

As used herein, the term "tissue cell" refers to any tissue cell in a body, e.g., a human or animal body, including, e.g., epithelium, muscle, nerve, and bone cells. Tissue cells do not include blood cells. As used herein, blood normally comprises plasma, red blood cells, white blood cells (including leukocytes and lymphocytes), and platelets. Leukocytes include neutrophils, monocytes, eosinophils and basophils, and lymphocytes include T cells, B cells and natural killer cells.

As used herein, a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such a change in the nucleic acid molecule's nucleotide sequence can result in a nucleic acid molecule in which each methylated nucleotide is modified to a different nucleotide. Such a change in the nucleic acid nucleotide sequence can result in a nucleic acid molecule in which each unmethylated nucleotide is modified to a different nucleotide. Such a change in the nucleic acid nucleotide sequence can result in a nucleic acid molecule in which each of a selected nucleotide which is unmethylated (e.g., each unmethylated cytosine) is modified to a different nucleotide. Use of such a reagent to change the nucleic acid nucleotide sequence can result in a nucleic acid molecule in which each nucleotide that is a methylated nucleotide (e.g., each methylated cytosine) is modified to a different nucleotide. As used herein, use of a reagent that modifies a selected nucleotide refers to a reagent that modifies one nucleotide of the four typically occurring nucleotides in a nucleic acid molecule (C, G, T, and A for DNA and C, G, U, and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkylenglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) *Cancer Research* 57: 594-599.

The term "MethyLight™" refers to the art-recognized fluorescence-based real-time PCR technique described by Eads et al. (1999) *Cancer Res.* 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "Ms-SNuPE" (Methylation-sensitive Single Nucleotide Primer Extension) refers to the art-recognized assay described by Gonzalgo & Jones (1997) *Nucleic Acids Res.* 25: 2529-2531.

The term "MSP" (Methylation-specific PCR) refers to the art-recognized methylation assay described by Herman et al. (1996) *Proc. Natl. Acad. Sci. USA* 93: 9821-9826, and by U.S. Pat. No. 5,786,146.

The term "COBRA" (Combined Bisulfite Restriction Analysis) refers to the art-recognized methylation assay described by Xiong & Laird (1997) *Nucleic Acids Res.* 25: 2532-2534.

The term "MCA" (Methylated CpG Island Amplification) refers to the methylation assay described by Toyota et al. (1999) *Cancer Res.* 59: 2307-12, and in WO 00/26401A1.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides.

The term "system" as used herein refers to a collection of articles for use for a particular purpose. In some embodiments, the articles comprise instructions for use, as information supplied on e.g., an article, on paper, or on recordable media (e.g., DVD, CD, flash drive, etc.). In some embodiments, instructions direct a user to an online location, e.g., a website.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DETAILED DESCRIPTION

Provided herein is technology relating to performing assays for detection and quantification of DNA, e.g., methylated DNA. In particular, the technology relates to internal controls for such methylation assays.

Embodiments of the present disclosure provide a marker termed "B3GALT6" for use as a methylation marker and internal control. The β-actin (ACTB) gene is often used as an internal control target in assays that detect methylated DNA. However, ACTB does not contain methylated CpG islands and, thus, upon bisulfite conversion lose all cytosine residues, which results in a highly AT rich sequence that can be problematic for primer and probe design (e.g., for multiplex assays with DNAs having a higher G-C content, longer probes and primers must be must be used to achieve the same Tm range for ACTB, and the reduced sequence complexity of converted ACTB increases the risk of cross-reactivity of primers and probes with other DNA in the reaction). Further, it has been determined that ACTB DNA undergoes bisulfite conversion at a faster rate than do methylated DNA markers, which makes it difficult to achieve optimized bisulfite conversion parameters for both the ACTB marker and methylated DNA markers in the same sample.

During development of the present technology, it was determined that B3GALT6 is highly methylated DNA that may be used as an alternative control DNA. During development of the technology it was determined that B3GALT6 DNA behaves similarly to methylated marker DNAs during bisulfite conversion. As the methylated Cs are not converted during bisulfite treatment, use of a methylated DNA as an internal control DNA in place of β-actin provides an internal control that maintains its sequence complexity upon conversion, and that permits use of shorter oligonucleotides in DNA detection assays, e.g., PCR and/or flap endonuclease assays such as the QuARTS assay described hereinbelow.

Although the disclosure herein refers to certain illustrated embodiments, it is to be understood that these embodiments are presented by way of example and not by way of limitation.

I. Methylated Control Genes

In assays that detect and quantify methylated CpG-rich DNA that has undergone bisulfite conversion, it is typical to also detect a control gene present in the same sample, the control gene verifying the DNA input in the assay regardless of source (e.g., cancer, normal, stool, tissue). Such a control gene is used, for example, to normalize DNA copy number data obtained in assays across different samples, to accurately show higher or lower disease-associated marker levels sample-to-sample.

For a methylation assay normalizing gene to work best, it should meet several criteria. An ideal normalizing gene, for example: 1) should be equally present in both normal and diseased tissue; 2) should have approximately the same GC content as the test gene(s)/marker(s) that are being assayed (e.g., DNA markers in which hypermethylation is an indicator of a disease state); 3) should react in the same manner as the test genes/markers to pre-quantification (pre-PCR) sample treatments, such as bisulfite conversion; and 4) should have PCR amplification efficiency that is similar to that of the test genes/markers being assayed.

The β-actin gene, a gene typically used as a normalizing gene for detection of methylated marker DNAs, does not have the same GC content and CpG methylation as methylation markers associated with diseases such as cancer and adenoma (e.g., vimentin, septin 9, NDRG4, BMP3), so it does not behave like such marker DNAs in pre-PCR bisulfite conversion or in PCR amplification.

Experiments described herein identified genes (e.g., B3GALT6) that are highly methylated in normal and cancer tissue and in white blood cells. The genes described herein are used to normalize marker levels across patients and samples.

II. Methylation Detection Assays

The markers described herein (e.g., B3GALT6, in particular), find use in a variety of methylation detection assays as normalization reagents and indicators of disease states.

The most frequently used method for analyzing a nucleic acid for the presence of 5-methylcytosine is based upon the bisulfite method described by Frommer, et al. for the detection of 5-methylcytosines in DNA (Frommer et al. (1992) Proc. Natl. Acad. Sci. USA 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is disulfonated under alkaline conditions to form uracil. Detection is possible because uracil base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98), methylation-specific PCR (MSP) as is disclosed, e.g., in U.S. Pat. No. 5,786,146, or using an assay comprising sequence-specific probe cleavage, e.g., a QuARTS flap endonuclease assay (see, e.g., Zou et al. (2010) "Sensitive quantification of methylated markers with a novel methylation specific technology" *Clin Chem* 56: A199; U.S. Pat. No. 8,361,720, and U.S. patent application Ser. Nos. 12/946,745; 12/946,752, and 61/705,603).

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" *Nucleic Acids Res.* 24: 5064-6). It is thus possible to analyze individual cells for methylation status, illustrating the utility and sensitivity of the method. An overview of conventional methods for detecting 5-methylcytosine is provided by Rein, T., et al. (1998) *Nucleic Acids Res.* 26: 2255.

The bisulfite technique typically involves amplifying short, specific fragments of a known nucleic acid subsequent to a bisulfite treatment, then either assaying the product by sequencing (Olek & Walter (1997) *Nat. Genet.* 17: 275-6) or a primer extension reaction (Gonzalgo & Jones (1997) *Nucleic Acids Res.* 25: 2529-31; WO 95/00669; U.S. Pat. No. 6,251,594) to analyze individual cytosine positions. Some methods use enzymatic digestion (Xiong & Laird (1997) *Nucleic Acids Res.* 25: 2532-4). Detection by hybridization has also been described in the art (Olek et al., WO 99/28498). Additionally, use of the bisulfite technique for methylation detection with respect to individual genes has been described (Grigg & Clark (1994) *Bioessays* 16: 431-6; Zeschnigk et al. (1997) *Hum Mol Genet.* 6: 387-95; Feil et al. (1994) *Nucleic Acids Res.* 22: 695; Martin et al. (1995) *Gene* 157: 261-4; WO 9746705; WO 9515373).

Various methylation assay procedures can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) *Proc. Natl. Acad. Sci. USA* 89: 1827-1831). Additionally, restriction enzyme digestion of PCR products amplified from bisulfite-converted DNA finds use in assessing methylation state, e.g., as described by Sadri & Hornsby (1997) *Nucl. Acids Res.* 24: 5058-5059 or as embodied in the method known as COBRA (Combined Bisulfite Restriction Analysis) (Xiong & Laird (1997) *Nucleic Acids Res.* 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can be used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" *Nat Methods* 7: 133-6; Meissner et al. (2005) "Reduced representation bisulfite sequencing for comparative high-resolution DNA methylation analysis" *Nucleic Acids Res.* 33: 5868-77.

In some embodiments, a quantitative allele-specific real-time target and signal amplification (QUARTS) assay is used to evaluate methylation state. Three reactions sequentially occur in each QuARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes a 5' nuclease, e.g., a FEN-1 endonuclease, to release the flap sequence by cutting between the detection probe and the flap sequence. The flap sequence is complementary to a non-hairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" *Clin Chem* 56: A199).

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkylenglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

In some embodiments, the bisulfite-treated DNA is purified prior to the quantification. This may be conducted by any means known in the art, such as but not limited to ultrafiltration, e.g., by means of Microcon™ columns (manufactured by Millipore™). The purification is carried out according to a modified manufacturer's protocol (see, e.g., PCT/EP2004/011715, which is incorporated by reference in its entirety). In some embodiments, the bisulfite treated DNA is bound to a solid support, e.g., a magnetic bead, and desulfonation and washing occurs while the DNA is bound to the support. Examples of such embodiments are provided, e.g., in WO 2013/116375. In certain preferred embodiments, support-bound DNA is ready for a methylation assay immediately after desulfonation and washing on the support. In some embodiments, the desulfonated DNA is eluted from the support prior to assay.

In some embodiments, fragments of the treated DNA are amplified using sets of primer oligonucleotides according to the present invention (e.g., see Table 2) and an amplification enzyme. The amplification of several DNA segments can be carried out simultaneously in one reaction vessel. Typically, the amplification is carried out using a polymerase chain reaction (PCR).

In another embodiment of the method, the methylation status of CpG positions within or near a marker are detected by use of methylation-specific primer oligonucleotides. This technique (MSP) has been described, e.g., in U.S. Pat. Nos. 5,786,146 and 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position corresponding to the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better detectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids", published as US 2012/0288868), incorporated herein by reference in its entirety.

In some embodiments, the markers described herein find use in QUARTS assays performed on stool samples. In some embodiments, methods for producing DNA samples and, in particular, to methods for producing DNA samples that comprise highly purified, low-abundance nucleic acids in a small volume (e.g., less than 100, less than 60 microliters) and that are substantially and/or effectively free of substances that inhibit assays used to test the DNA samples (e.g., PCR, INVADER, QuARTS assays, etc.) are provided. Such DNA samples find use in diagnostic assays that qualitatively detect the presence of, or quantitatively measure the activity, expression, or amount of, a gene, a gene variant (e.g., an allele), or a gene modification (e.g., methylation) present in a sample taken from a patient. For example, some cancers are correlated with the presence of particular mutant alleles or particular methylation states, and thus detecting and/or quantifying such mutant alleles or methylation states has predictive value in the diagnosis and treatment of cancer.

Many valuable genetic markers are present in extremely low amounts in samples and many of the events that produce such markers are rare. Consequently, even sensitive detection methods such as PCR require a large amount of DNA to provide enough of a low-abundance target to meet or supersede the detection threshold of the assay. Moreover, the presence of even low amounts of inhibitory substances compromise the accuracy and precision of these assays directed to detecting such low amounts of a target. Accordingly, provided herein are methods providing the requisite management of volume and concentration to produce such DNA samples.

Some biological samples, such as stool samples, contain a wide variety of different compounds that are inhibitory to PCR. Thus, the DNA extraction procedures include methods to remove and/or inactivate PCR inhibitors. As such, in some embodiments, processing and preparing samples and particularly, but not exclusively, to methods, systems, and kits for removing assay inhibitors from samples comprising nucleic acids are described in Example 1.

In some embodiments, the sample comprises blood, serum, plasma, gastric secretions, pancreatic juice, a biopsy samples, e.g., from gastrointestinal, lung, and other cancers, microdissected cells from a biopsy, cells sloughed into the lumen, and/or cells recovered from stool. In some embodiments, the subject is human. The sample may include cells, secretions, or tissues from, for example, the lung, liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample.

Such samples can be obtained by any number of means known in the art, such as will be apparent to the skilled person. For instance, urine and fecal samples are easily attainable, while blood, ascites, serum, or pancreatic fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Nos. 8,808,990 and 9,169,511, and in WO 2012/155072, or by a related method.

The analysis of markers can be carried out separately or simultaneously with additional markers within one test sample. For example, several markers can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

III. Other Applications

In some embodiments, diagnostic assays identify the presence of a disease or condition in an individual. In some embodiments, the disease is cancer (e.g., lung cancer, liver cancer, cancer of the gastrointestinal system).

The present disclosure is not limited to particular markers. In some embodiments, markers whose aberrant methylation is associated with a neoplasm are utilized (e.g., one or more of vimentin, septin 9, NDRG4; see also U.S. Prov. Patent App. No. 62/091,053, filed Dec. 12, 2014, which is incorporated by reference herein in its entirety, for all purposes). In some embodiments, an assay further comprises detection of mutated KRAS genes (See e.g., Example 1). In some embodiments, assays further comprise detection of hemoglobin in stool samples (See e.g., Example 1).

In some embodiments, the technology relates to a method for treating a patient (e.g., a patient with cancer, with early stage cancer, or who may develop cancer), the method comprising determining the methylation state of one or more markers as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments of the technology, a method for diagnosing a cancer in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., those described herein), the methylation state of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., those described herein) disclosed herein. Further, in some embodiments of the presently disclosed subject matter, multiple determinations of the biomarkers over time can be made to facilitate diagnosis and/or prognosis. A temporal change in the biomarker can be used to predict a clinical outcome, monitor the progression of cancer, and/or monitor the efficacy of appropriate therapies directed against the cancer. In such an embodiment for example, one might expect to see a change in the methylation state of one or more biomarkers disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with cancer risk, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more target genes), the chance of a given outcome (e.g., suffering from a cancer) may be very low.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein can be established, and the degree of change in the methylation state of the biomarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with a cancer. In certain embodiments of the method, a subject is identified as having metaplasia upon identifying an aberrant methylation state of one or more markers provided herein in a biological sample obtained from the subject. In other embodiments of the method, the detection of an aberrant methylation state of one or more of such biomarkers in a biological sample obtained from the subject results in the subject being identified as having cancer.

In some embodiments, the subject is diagnosed as having a cancer if, when compared to a control methylation state, there is a measurable difference in the methylation state of at least one biomarker in the sample. Conversely, when no change in methylation state is identified in the biological sample, the subject can be identified as not having cancer, not being at risk for the cancer, or as having a low risk of the cancer. In this regard, subjects having the cancer or risk thereof can be differentiated from subjects having low to substantially no cancer or risk thereof. Those subjects having a risk of developing a particular cancer, e.g., gastrointestinal cancer, can be placed on a more intensive and/or regular screening schedule, including, e.g., endoscopic surveillance. On the other hand, those subjects having low to substantially no risk may avoid being subjected to invasive screening methods such as endoscopy, until such time as a future screening, for example, a screening conducted in accordance with the present technology, indicates that a risk of cancer has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, a cancer indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds, and horses. Thus, also provided is the diagnosis and treatment of livestock, including, but not limited to, domesticated swine, ruminants, ungulates, horses (including race horses), and the like. The presently-disclosed subject matter further includes a system for diagnosing a gastrointestinal, lung, or other cancers in a subject. The system can be provided, for example, as a commercial kit that can be used to screen for a risk of cancer or diagnose a cancer in a subject from whom a biological sample has been collected. An exemplary system provided in accordance with the present technology includes assessing the methylation state of a marker described herein.

In certain embodiments, the compositions, reaction mixtures, and/or methods described herein find use in a variety of diagnostic, medical, analytical, and research applications, and the invention should not be viewed as limited to any particular field or use. However, in particular embodiments, the present invention finds use in the analysis, detection, characterization, etc. of nucleic acid (e.g., human nucleic acid, target nucleic acid, etc.) from stool. Compositions, methods, devices, etc. for use in the embodiments described herein are found in, for example, U.S. Pat. Nos. 8,361,720; 7,981,612; 7,368,233; 6,964,846; 6,919,174; 6,849,403; 6,844,155; 6,818,404; 6,750,020; 6,586,177; 6,551,777; 6,503,718; 6,498,012; 6,482,595; 6,475,738; 6,428,964; 6,415,455; 6,406,857; 6,351,857; 6,303,304; 6,300,077; 6,280,947; 6,268,136; 6,203,993; 6,146,828; 6,143,529; 6,020,137; 5,952,178; 5,928,870; 5,888,778; 5,830,665; 5,741,650; 5,670,325; each of which is herein incorporated by reference in its entirety for any purpose. In certain embodiments, the compositions and methods described herein find use in, for example, a quantitative allele-specific real-time target and signal amplification assay (QUARTS assay), as described in, e.g., in U.S. Pat. Nos. 8,361,720; 8,715,937; 8,916,344; and 9,212,392.

EXPERIMENTAL

During the development of embodiments of technology related to tests for cancer, e.g., lung cancer, experiments suggested that using a methylated control DNA would provide an improved test. Accordingly, technologies are provided herein comprising methylated DNA control targets that generate specific signals when processed and detected in parallel with experimental targets (e.g., methylated marker genes) in a sample (e.g., from a patient). In particular, the controls provided herein comprise various nucleic acid targets that are extracted from a sample in parallel with one or more marker DNAs, that are converted during the bisulfate conversion, and that present a converted sequence for detection by nucleic acid detection assays, e.g., QUARTS methylation assays.

Example 1

Sample Preparation Methods

Methods for DNA Isolation and QUARTS Assay

The following provides exemplary method for DNA isolation prior to analysis, and an exemplary QUARTS assay, such as may be used in accordance with embodiments of the technology. Application of QuARTS technology to DNA from stool and various tissue samples is described in this example, but the technology is readily applied to other nucleic acid samples, e.g., as shown in other examples.

Optionally, zebrafish DNA, e.g., synthetic DNA prepared as described in U.S. Provisional Patent Appl. Ser. No. 62/364,049 may be added to the samples as described herein as a run control for the isolation, bisulfate-conversion and/or the DNA detection assay. For example, 100 µl of 120 copies/µL, of synthetic methylated zebrafish DNA in 0.4 ng/µl of fish DNA diluent (bulk genomic DNA isolated from salmon, cod and/or herring, as described, e.g., in U.S. Pat. No. 9,212,392) may be added to a sample, e.g., a plasma sample, prior to addition of a lysis buffer, before or after the addition of Proteinase K, etc. and detected along with marker and reference DNAs.

Collection of Target DNA from Stool Samples.

Whole stools are collected in plastic buckets. A preservative buffer, e.g., 150 mM EDTA, 500 mM Tris-Cl and 10 mM NaCl, (pH 9.0) is added to the stool, e.g., at about 4 ml per gram of stool, and buffered stools may be used directly or archived at −80° C.

Exemplary procedure for isolation of target nucleic acids from stool samples:

1. A stool sample is homogenized, e.g., with a buffer, to form a stool homogenate. The homogenate treated to partition residual solids from the fluid, e.g., by centrifugation or filtration, to produce a "stool supernatant."
2. Stool supernatant is treated to remove assay inhibitors (e.g., with polyvinylpolypyrrolidone, as described in U.S. Pat. No. 8,993,341, which is incorporated herein by reference in its entirety), producing "clarified supernatant".
3. Ten milliliters of clarified supernatant (representing an equivalent of approximately 4 grams of stool) is mixed with guanidine thiocyanate (GTC) to a final concentration of 2.4 M;
4. The mixture is then heated in a 90° C. water bath for 10 minutes to denature the DNA (and proteins) present in the stool.
5. Paramagnetic particles containing covalently attached (coupled) oligonucleotides complementary to the target sequence(s) of interest ("target-specific capture probes") are added to the sample. The sample is then incubated (e.g., at ambient temperature, about 22-25° C.) for one hour to enable hybridization of the target DNA to the capture probes on the magnetic particles.
6. The mixture of clarified supernatant, GTC, and particles is exposed to a magnetic field to separate the particles (now containing target DNA hybridized to the capture probes) from the stool supernatant/GTC mixture, which is transferred to a new tube. See, e.g., U.S. patent application Ser. No. 13/089,116, which is incorporated herein by reference.

The denaturation/hybridization/separation cycle (steps 4-6) can be repeated, e.g., least four or more times to serially extract different target DNAs from the same stool supernatant sample.

FFPE Tissue DNA

DNA from formalin-fixed, paraffin-embedded (FFPE) tissue is isolated using the QIAamp DNA FFPE Tissue Kit (Qiagen Sciences, Germantown, Md.).

DNA Isolation from Cells and Plasma

For cell lines, genomic DNA may be isolated from cell conditioned media using, for example, the "Maxwell® RSC ccfDNA Plasma Kit (Promega Corp., Madison, Wis.). Following the kit protocol, 1 mL of cell conditioned media (CCM) is used in place of plasma, and processed according to the kit procedure.

An alternative exemplary procedure for isolating DNA from plasma is as follows:

To a 4 mL sample of plasma, 300 µL of Proteinase K (20 mg/mL) is added and mixed.

Add 3 µL of 1 µg/µL of fish DNA diluent to the plasma-proteinase K mixture.

Add 2 mL of plasma lysis buffer to plasma.
Plasma lysis buffer is:
4.3M guanidine thiocyanate
10% IGEPAL CA-630 (Octylphenoxy poly(ethyl-eneoxy)ethanol, branched)
(5.3 g of IGEPAL CA-630 combined with 45 mL of 4.8 M guanidine thiocyanate)

Incubate mixtures at 55° C. for 1 hour with shaking at 500 rpm.

Add 3 mL of plasma lysis buffer and mix.

Add 200 µL magnetic silica binding beads (16 µg of beads/µL} and mix again.

Add 2 mL of 100% isopropanol and mix.

Incubate at 30° C. for 30 minutes with shaking at 500 rpm.

Place tube(s) on magnet and let the beads collect. Aspirate and discard the supernatant.

Add 7504 GuHCl-EtOH to vessel containing the binding beads and mix. GuHCl-EtOH wash buffer is:
3M GuHCl (guanidine hydrochloride)
57% EtOH (ethyl alcohol)

Shake at 400 rpm for 1 minute.

Transfer samples to a deep well plate or 2 mL microcentrifuge tubes.

Place tubes on magnet and let the beads collect for 10 minutes. Aspirate and discard the supernatant.

Add 1000 µL wash buffer (10 mM Tris HCl, 80% EtOH) to the beads, and incubate at 30° C. for 3 minutes with shaking.

Place tubes on magnet and let the beads collect. Aspirate and discard the supernatant.

Add 500 µL wash buffer to the beads and incubate at 30° C. for 3 minutes with shaking.

Place tubes on magnet and let the beads collect. Aspirate and discard the supernatant.

Add 250 µL wash buffer and incubate at 30° C. for 3 minutes with shaking.

Place tubes on magnet and let the beads collect. Aspirate and discard the remaining buffer.

Add 250 µL wash buffer and incubate at 30° C. for 3 minutes with shaking.

Place tubes on magnet and let the beads collect. Aspirate and discard the remaining buffer.

Dry the beads at 70° C. for 15 minutes, with shaking.

Add 125 µL elution buffer (10 mM Tris HCl, pH 8.0, 0.1 nM EDTA) the beads and incubate at 65° C. for 25 minutes with shaking.

Place tubes on magnet and let the beads collect for 10 minutes.

Aspirate and transfer the supernatant containing the DNA to a new vessel or tube.

Bisulfite Conversion of DNA

DNA for methylation testing is treated with bisulfite using, e.g., the EZ-96 DNA Methylation Kit (Zymo Research, Irvine Calif.) or using ammonium hydrogen sulfite as described in U.S. Pat. No. 9,315,853 and in U.S. Prov. Patent Appl. No. 62/249,097, each of which is incorporated herein by reference in its entirety.

An exemplary method of treating DNA with a bisulfite reagent to convert unmethylated cytosine residues is as follow:

I. Sulfonation of DNA Using Ammonium Hydrogen Sulfite
1. In each tube, combine 64 µL DNA, 7 µL 1 N NaOH, and 9 µL of carrier solution containing 0.2 mg/mL BSA and 0.25 mg/mL of fish DNA.
2. Incubate at 42° C. for 20 minutes.
3. Add 120 µL of 45% ammonium hydrogen sulfite and incubate at 66° for 75 minutes.
4. Incubate at 4° C. for 10 minutes.

II. Desulfonation Using Magnetic Beads
Materials
Magnetic beads (Promega MagneSil Paramagnetic Particles, Promega catalogue number AS1050, 16 µg/µL).
Binding buffer: 6.5-7 M guanidine hydrochoride.
Post-conversion Wash buffer: 80% ethanol with 10 mM Tris HCl (pH 8.0).
Desulfonation buffer: 70% isopropyl alcohol, 0.1 N NaOH was selected for the desulfonation buffer.

Samples are mixed using any appropriate device or technology to mix or incubate samples at the temperatures and mixing speeds essentially as described below. For example, a Thermomixer (Eppendorf) can be used for the mixing or incubation of samples. An exemplary desulfonation is as follows:
1. Mix bead stock thoroughly by vortexing bottle for 1 minute.
2. Aliquot 50 µL of beads into a 2.0 mL tube (e.g., from USA Scientific).
3. Add 750 µL of binding buffer to the beads.
4. Add 150 µL of sulfonated DNA from step I.
5. Mix (e.g., 1000 RPM at 30° C. for 30 minutes).
6. Place tube on the magnet stand and leave in place for 5 minutes. With the tubes on the stand, remove and discard the supernatant.
7. Add 1,000 µL of wash buffer. Mix (e.g., 1000 RPM at 30° C. for 3 minutes).
8. Place tube on the magnet stand and leave in place for 5 minutes. With the tubes on the stand, remove and discard the supernatant.
9. Add 250 µL of wash buffer. Mix (e.g., 1000 RPM at 30° C. for 3 minutes).
10. Place tube on magnetic rack; remove and discard supernatant after 1 minute.
11. Add 200 µL of desulfonation buffer. Mix (e.g., 1000 RPM at 30° C. for 5 minutes).
12. Place tube on magnetic rack; remove and discard supernatant after 1 minute.
13. Add 250 µL of wash buffer. Mix (e.g., 1000 RPM at 30° C. for 3 minutes).
14. Place tube on magnetic rack; remove and discard supernatant after 1 minute.
15. Add 250 µL of wash buffer to the tube. Mix (e.g., 1000 RPM at 30° C. for 3 minutes).
16. Place tube on magnetic rack; remove and discard supernatant after 1 minute.
17. Incubate all tubes at 30° C. with the lid open for 15 minutes.
18. Remove tube from magnetic rack and add 70 µL of elution buffer directly to the beads.
19. Incubate the beads with elution-buffer (e.g., 1000 RPM at 40° C. for 45 minutes).
20. Place tubes on magnetic rack for about one minute; remove and save the supernatant.

The converted DNA is then used in pre-amplification and/or flap endonuclease assays, as described below.

QuARTS Flap Endonuclease Assay

The QUARTS technology combines a polymerase-based target DNA amplification process with an invasive cleavage-based signal amplification process. The technology is described, e.g., in U.S. Pat. Nos. 8,361,720; 8,715,937; 8,916,344; and 9,212,392, each of which is incorporated herein by reference. Fluorescence signal generated by the QUARTS reaction is monitored in a fashion similar to real-time PCR and permits quantitation of the amount of a target nucleic acid in a sample.

An exemplary QuARTS reaction typically comprises approximately 400-600 nmol/l (e.g., 500 nmol/1) of each primer and detection probe, approximately 100 nmol/l of the invasive oligonucleotide, approximately 600-700 nmol/l of each FRET cassette (FAM, e.g., as supplied commercially by Hologic, Inc.; HEX, e.g., as supplied commercially by BioSearch Technologies; and Quasar 670, e.g., as supplied commercially by BioSearch Technologies), 6.675 ng/µl FEN-1 endonuclease (e.g., Cleavase® 2.0, Hologic, Inc.), 1 unit Taq DNA polymerase in a 30 µl reaction volume (e.g., GoTaq® DNA polymerase, Promega Corp., Madison, Wis.), 10 mmol/l 3-(n-morpholino) propanesulfonic acid (MOPS), 7.5 mmol/1 $MgCl_2$, and 250 µmol/l of each dNTP. Exemplary QuARTS cycling conditions are as shown in the table below. In some applications, analysis of the quantification cycle ($C_q$) provides a measure of the initial number of target DNA strands (e.g., copy number) in the sample.

| Stage | Temp/Time | # of Cycles |
|---|---|---|
| Denaturation | 95° C./3' | 1 |
| Amplification 1 | 95° C./20" | 10 |
| | 67° C./30" | |
| | 70° C./30" | |

-continued

| Stage | Temp/Time | # of Cycles |
|---|---|---|
| Amplification 2 | 95° C./20"<br>53° C./1'<br>70° C./30" | 37 |
| Cooling | 40° C./30" | 1 |

Multiplex Targeted Pre-Amplification of Large-Volume Bisulfite-Converted DNA

To pre-amplify most or all of the bisulfite treated DNA from an input sample, a large volume of the treated DNA may be used in a single, large-volume multiplex amplification reaction. For example, DNA is extracted from a cell line (e.g., DFCI032 cell line (adenocarcinoma); H1755 cell line (neuroendocrine)), using, for example, the Maxwell Promega blood kit #AS1400, as described above. The DNA is bisulfite converted, e.g., as described above.

A pre-amplification is conducted, for example, in a reaction mixture containing 7.5 mM $MgCl_2$, 10 mM MOPS, 0.3 mM Tris-HCl, pH 8.0, 0.8 mM KCl, 0.1 μg/μL BSA, 0.0001% Tween-20, 0.0001% IGEPAL CA-630, 250 μM each dNTP, oligonucleotide primers, (e.g., for 12 targets, 12 primer pairs/24 primers, in equimolar amounts (including but not limited to the ranges of, e.g., 200-500 nM each primer), or with individual primer concentrations adjusted to balance amplification efficiencies of the different target regions), 0.025 units/μL HotStart GoTaq concentration, and 20 to 50% by volume of bisulfite-treated target DNA (e.g., 10 μL of target DNA into a 50 μL reaction mixture, or 50 μL of target DNA into a 125 μL reaction mixture). Thermal cycling times and temperatures are selected to be appropriate for the volume of the reaction and the amplification vessel. For example, the reactions may be cycled as follows

| Stage | Temp/Time | #of Cycles |
|---|---|---|
| Pre-incubation | 95° C./5' | 1 |
| Amplification 1 | 95° C./30"<br>64° C./30"<br>72° C./30" | 10 |
| Cooling | 4° C./Hold | 1 |

After thermal cycling, aliquots of the pre-amplification reaction (e.g., 10 μL) are diluted to 500 μL in 10 mM Tris-HCl pH8.0, 0.1 mM EDTA, with or without fish DNA. Aliquots of the diluted pre-amplified DNA (e.g., 10 μL) are used in a QUARTS PCR-flap assay, e.g., as described above. See also U.S. Patent Appl. Ser. No. 62/249,097, filed Oct. 30, 2015, which is incorporated herein by reference for all purposes.

Example 2

Test of B3GALT6 Assay on Bisulfite-Converted Human Genomic DNA and DNA Extracted from FFPE Colon Tissue Samples Bisulfite-Converted Universal Methylated Human DNA Standard, catalogue #D5015 (Zymo research) was diluted to 1 ng and 0.1 ng per μL in 20 ng/μL fish DNA. DNA from a colon tissue was extracted from FFPE slide-mounted samples using the Qiagen miniKit protocol and was treated with bisulfate using the Zymo EZ DNA conversion kit #D5001.

EcoRI-digested pUC57 plasmids containing an insert fragment having the sequence of bisulfate-converted B3GALT6 or of bisulfate-converted β-actin were diluted in 20 ng/μL fish DNA to levels of 2000, 200, 20, and 2 strands/μL.

Procedure:
1) Make the following 10× oligonucleotide mix and 20× Enzyme Mix:
   10× Oligo Mix 1 (B3GALT6 and β-Actin Biplex):

| Oligo | Final Concentration (μM) |
|---|---|
| B3GALT6 forward primer | 2 |
| B3GALT6 reverse primer | 2 |
| B3GALT6 Probe (Arm 5) | 5 |
| β-actin BT forward primer 1 | 2 |
| β-actin BT reverse primer 1 | 2 |
| β-actin BT Probe (Arm 3) | 5 |
| A3 QUASAR FRET cassette | 5 |
| A5 FAM FRET cassette | 5 |
| dNTPs | 2500 |

20× Enzyme Mix:
  200 mM MOPS, pH 7.5,
  150 mM $MgCl_2$,
  6.38 mM Tris-HCl, pH 8.0,
  15.94 mM KCl,
  2 μg/μL BSA,
  0.16% Tween-20,
  0.16% IGEPAL CA-630,
  25% Glycerol,
  146 ng/μL Cleavase 2.0,
  1 unit/μL HotStart GoTaq polymerase 2) Distribute the following to the wells in a 96 well plate:

| Component | μL Of Stock Reaction |
|---|---|
| 20X Enzyme Mix | 1.5 |
| 10X Oligo mix | 3 |
| Water | 15.5 |
| Sample* | 10 |
| total volume | 20 |

*For samples, add 10 uL of Zymo standard DNA at 1 ng/μL, 10 μL of Zymo standard at 0.1 ng/μL, or 10 μL of DNA extracted from tissue using the following plate layout:

| Oligo | B3GALT6/β-actin | | | |
|---|---|---|---|---|
| Mix | 1 | 2 | 3 | 4 |
| A | 20000 strands | 20000 strands | Zymo 10 ng | Zymo 10 ng |
| B | 200 strands | 200 strands | Zymo 1 ng | Zymo 1 ng |
| C | 20 strands | 20 strands | Tissue | Tissue |
| D | NTC | NTC | NTC | NTC |

3) Seal plate with optical seal and put into LightCycler 480 and run profile described below:

| QuARTS Reaction Cycle: | Temp/Time | Ramp Rate (° C. per second) | Number of Cycles | Signal Acquisition |
|---|---|---|---|---|
| Pre-incubation | 95° C./3' | 4.4 | 1 | none |
| Amplification 1 | 95° C./20" | 4.4 | 10 | none |
| | 63° C./30" | 2.2 | | none |
| | 70° C./30" | 4.4 | | none |

-continued

| QuARTS Reaction Cycle: | Temp/Time | Ramp Rate (° C. per second) | Number of Cycles | Signal Acquisition |
|---|---|---|---|---|
| Amplification 2 | 95° C./20" | 4.4 | 35 | none |
|  | 53° C./1' | 2.2 |  | single |
|  | 70° C./30" | 4.4 |  | none |
| Cooling | 40° C./30" | 2.2 | 1 | none |

4) Calculate the amounts of Zymo genomic DNA and of the DNA isolated from the tissues based on the calibrator plasmids present in each oligonucleotide mix. The data are summarized in the table below:

| Sample | B3GALT6 strands | B-actin strands |
|---|---|---|
| Bisulfite converted genomic DNA (~10 ng) | 1629 | 1847 |
| Bisulfite converted genomic DNA (~1 ng) | 310 | 277 |
| Colon Tissue ID 9559 (Normal colon) | 1832 | 3642 |

These data show that B3GALT6 signal is observed in both bulk genomic DNA and in DNA extracted from FFPE colon tissue samples.

Example 3

Test of B3GALT6 Assay on DNA Extracted from Cancer and Normal Tissue Samples

DNA was extracted from FFPE slides of 32 lung tissue samples using Qiagen miniKit protocol, with added zebrafish-rassf1 synthetic DNA as a process control. The samples were bisulfite-converted with ammonium bisulfite as described in Example 1. Plasmid calibrators of EcoRI-digested pUC57 containing inserts for the bisulfite-converted B3GALT6 or bisulfite-converted β-actin, diluted in 20 ng/μL fish DNA, were used for quantitative calibration. Triplex QuARTS assays were performed as described in Example 1.

The results are shown in FIG. 3. Good correlation is observed between B3GALT6 and β-actin in lung samples. As the assay detects DNA that has been protected from sequence conversion by methylation, the copy number differences between converted β-actin and B3GALT6 are consistent with different levels of methylation between β-actin and B3GALT6 (i.e., all of the β-actin DNA is unmethylated and is converted to a sequence that matches its assay primers and probes, whereas a fraction of the B3GALT6 is not methylated and the assay oligonucleotides designed to detect the methylated B3GALT6 DNA do not match the unmethylated, bisulfite-converted fraction).

Example 4

Test of B3GALT6 Assay on Plasma Samples

DNA was extracted from 118 plasma samples (4 mL each) from cancer and normal patients using silica-based extraction and was treated with bisulfite as described in Example 1. Plasmid calibrators of EcoRI-digested pUC57 containing inserted DNA having the sequences of bisulfite-converted B3GALT6 or β-actin, diluted in 20 ng/μL fish DNA, were used for quantitative calibration.

Figure 4:
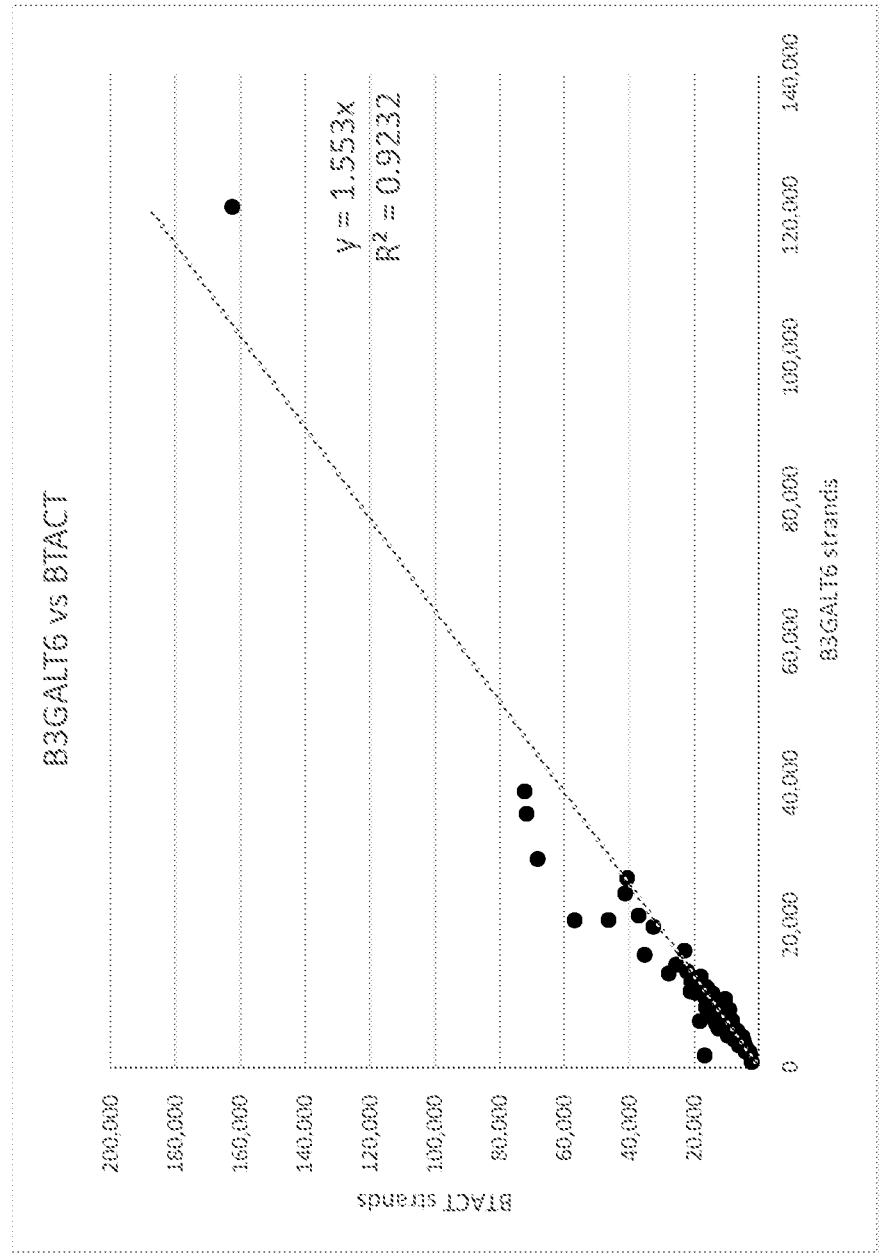
FIG. 4 provides a graph comparing the detection of bisulfate-converted B3GALT6 DNA to bisulfate-converted β-actin DNA in DNA extracted from 118 plasma samples, as described in Example 4.

The samples were assayed using the QuARTS assay as described in Example 1 and the results are shown in FIG. 4.

Good correlation is observed between B3GALT6 and β-actin in plasma samples regardless of the disease state of the subject from whom the samples are taken.

Example 5

Test of B3GALT6 Assay on Additional Plasma Samples

B3GALT6 was compared to β-actin as a reference target on an expanded set of samples comprising from both normal subjects and patients having lung cancer. DNA was extracted from a set of 297 plasma samples (2 mL) from cancer and normal patients using silica-based extraction and treated with bisulfite as described in Example 1. Plasmid calibrators of EcoRI-digested pUC57 containing inserted DNA having the sequence of bisulfite-converted B3GALT6 or bisulfite-converted β-actin, diluted in 20 ng/μL fish DNA, were used for quantitative calibration. Triplex QUARTS assays were performed as described for Multiplex QUARTS assays in Example 1, using 12 cycles in the initial amplification.

Figure 5:
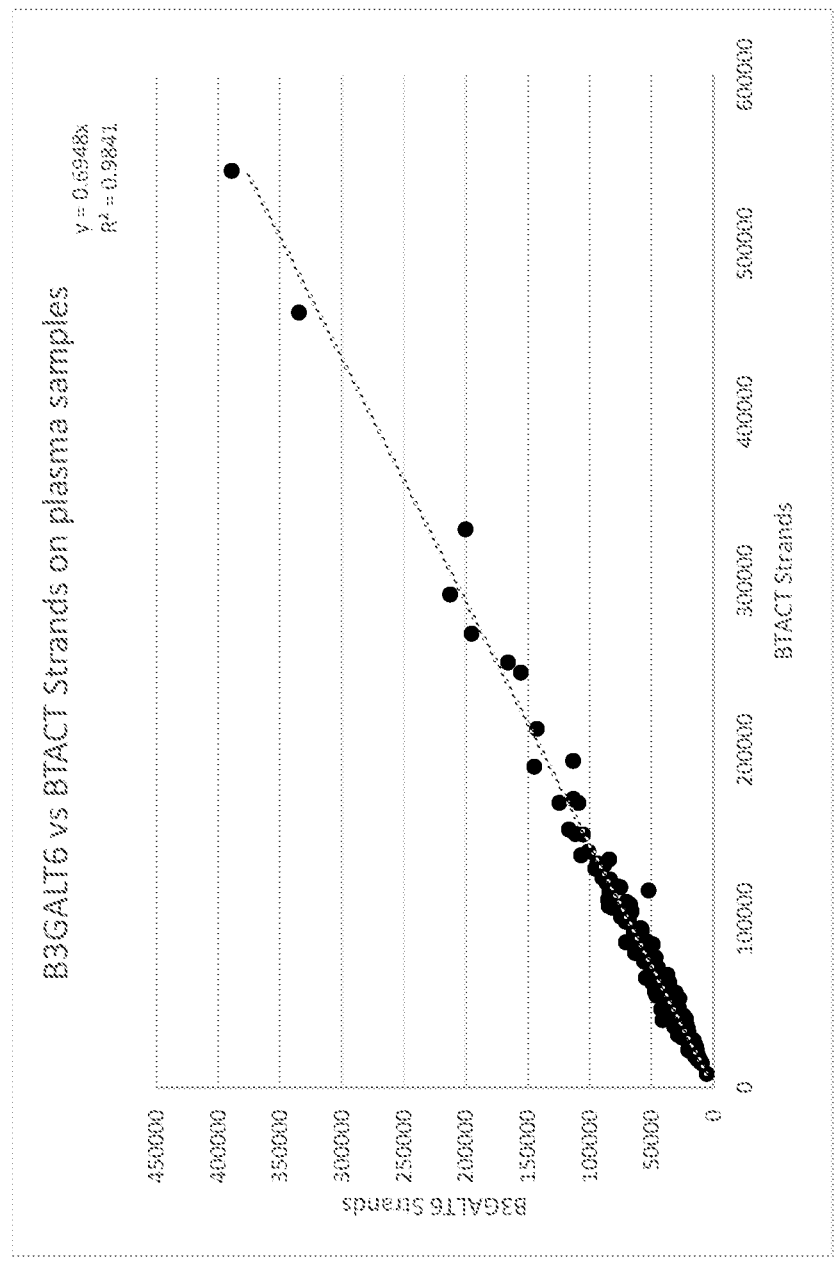
FIG. 5 provides a graph comparing the detection of bisulfate-converted B3GALT6 DNA to bisulfate-converted β-actin DNA in DNA extracted from 297 plasma samples, as described in Example 5.

The results are shown in FIG. 5, which compares the counts of detected strands for each of the B3GALT6 and β-actin targets. These data show that good correlation is observed between B3GALT6 and β-actin regardless of disease state, showing the suitability of B3GALT6 as a methylated reference gene.

Example 6

Figure 6A:
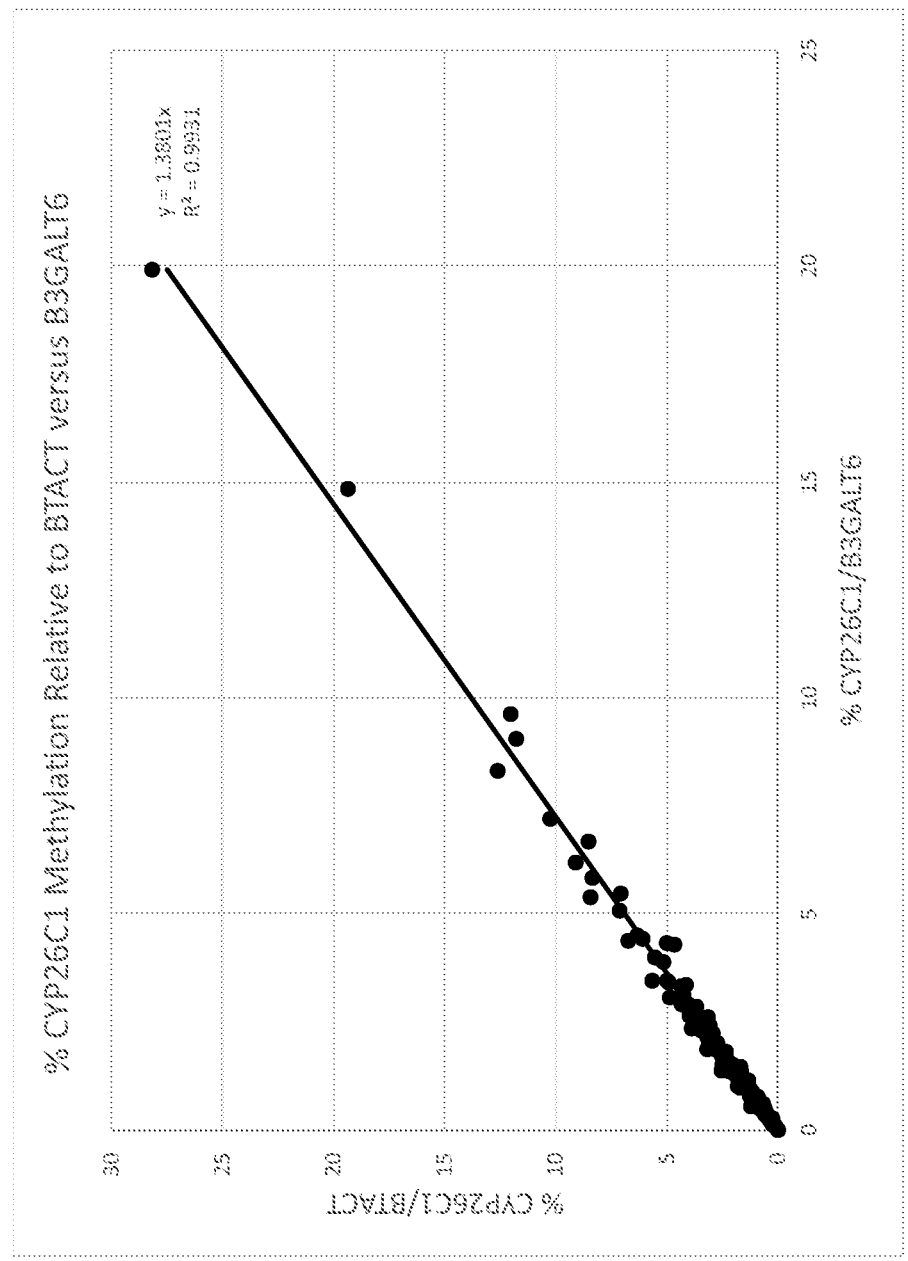
FIGS. 6A and 6B provide graphs comparing percent methylation of CYP26C1 and NFIX marker genes, respectively, in DNA extracted from 297 plasma samples, calculated using either bisulfate-converted B3GALT6 or bisulfate-converted β-actin as a reference gene, as described in Example 6.
Figure 6B:
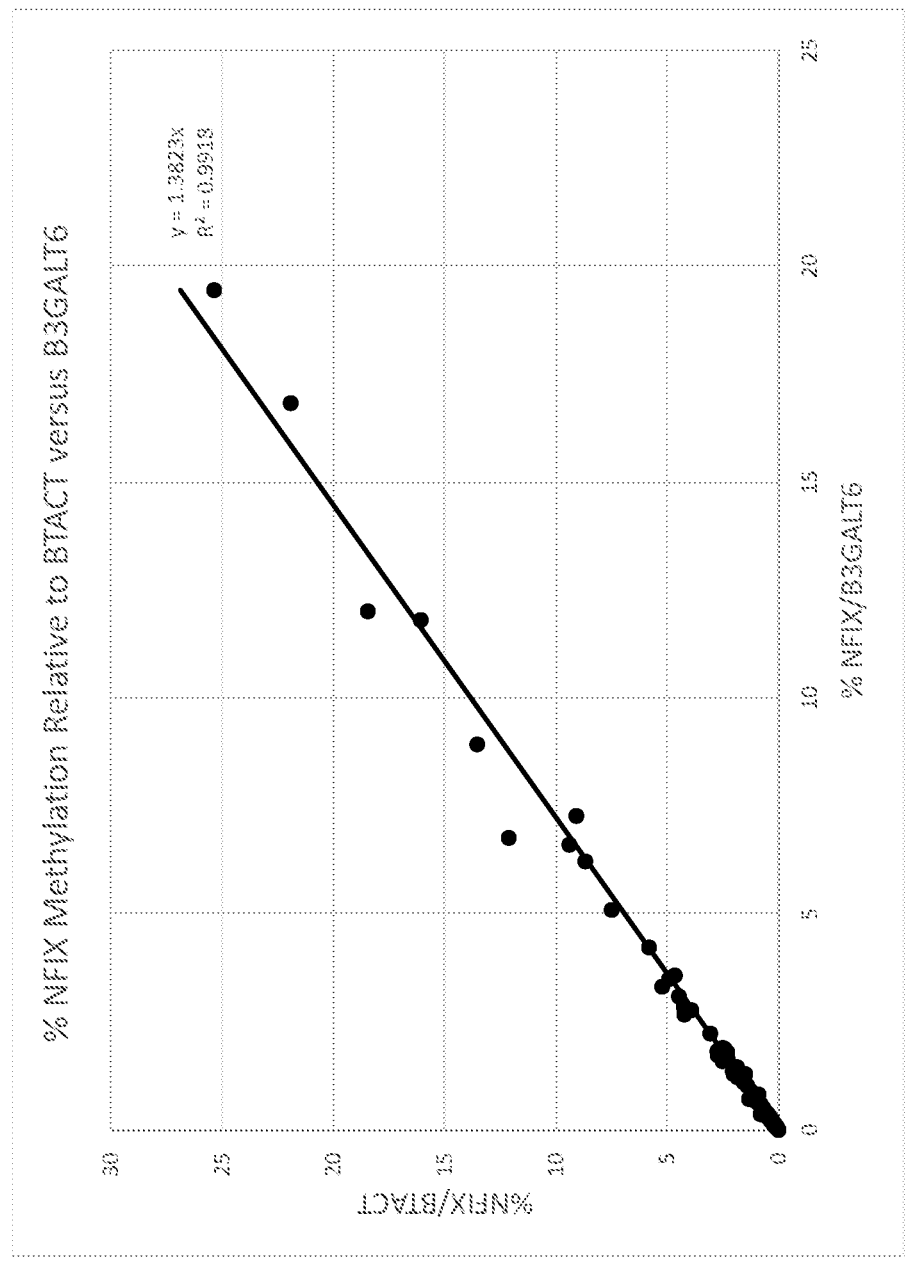

Comparing B3GALT6 and β-Actin as Reference Genes for Calculating % Methylation of Marker Genes The 297 plasma samples describe in Example 5 were further analyzed using the QuARTS assay for the present of methylation markers CYP26C1 and NFIX. FIGS. 6A and 6B compare bisulfate-treated β-actin or bisulfite-treated B3GALT6 as the reference for calculating the % methylation of these marker genes in the DNA from the plasma samples.

Example 7

Test of B3GALT6 as a Reference Gene in Lung Cells

Twenty lung cell lines were cultured and their DNA was extracted using the Qiagen Miniblood kit. The extracted DNA was treated with ammonium bisulfate as described in Example 1. Plasmid calibrators of EcoRI-digested pUC57 containing inserted DNA having the sequence of bisulfate-converted B3GALT6 or bisulfate-converted β-actin, diluted in 20 ng/μL fish DNA, were used for quantitative calibration. Multiplex QuARTS assays were performed as described in Example 1. The results, shown in the table below, demonstrate that the B3GALT6 reference marker is present in all lung cell types tested.

| SampleID | Cell Line Type | B3GALT6 | B-actin |
|---|---|---|---|
| A549 | Adeno | 569 | 876 |
| H2228 | Adeno | 578 | 1016 |
| DFCI032 | Adeno | 1075 | 962 |
| PC-9 | Adeno (EGFR del) | 695 | 936 |
| H1975 | Adeno (EGFR mut) | 389 | 778 |

| SampleID | Cell Line Type | B3GALT6 | B-actin |
|---|---|---|---|
| H23 | NSC Adeno | 902 | 869 |
| H1299 | Large cell | 532 | 339 |
| HCC4017 | Large cell | 1345 | 1364 |
| H1755 | Neuroendocrine | 616 | 733 |
| HCC1833 | Neuroendocrine | 1272 | 1077 |
| H1385 | Neuroendocrine | 446 | 1281 |
| DMS-53 | Small Cell | 807 | 982 |
| H69AR | Small Cell | 1165 | 1210 |
| DMS79 | Small Cell | 1652 | 1384 |
| H520 | Squamous | 832 | 882 |
| H1703 | Squamous | 1044 | 1109 |
| H2170 | Squamous | 514 | 749 |
| 2KT | Normal | 16516 | 20451 |
| 3KT | Normal | 14878 | 14519 |
| 30KT | Normal | 9995 | 13493 |

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A composition, comprising:
   a) a bisulfite-converted B3GALT6 DNA comprising SEQ ID NO:2 or the full complement of SEQ ID NO:2, and
   b) a pair of primers complementary to primer binding sites within SEQ ID NO:2 or the complement thereof.

2. The composition of claim 1, further comprising a detection probe oligonucleotide, wherein the detection probe oligonucleotide comprises a region that is complementary to a portion of said DNA.

3. The composition of claim 1, further comprising one or more of:
   a detection probe oligonucleotide;
   a FRET cassette;
   a FEN-1 endonuclease;
   a thermostable DNA polymerase.

4. The composition of claim 2, wherein said detection probe oligonucleotide comprises a reporter molecule.

5. The composition of claim 2, wherein said detection probe oligonucleotide comprises a flap sequence.

6. The composition of claim 4, where said reporter molecule comprises a fluorophore.

7. A method, the method comprising:
   a) treating DNA from a sample with a bisulfite reagent to produce a bisulfite-converted B3GALT6 DNA;
   b) amplifying a region of said bisulfite-converted DNA using a pair of nucleic acid primers; and
   c) detecting an amplified B3GALT6 DNA comprising SEQ ID NO:2 or the full complement thereof.

8. The method of claim 7, further comprising a step of detecting the amplified bisulfite-converted B3ALT6 DNA comprising SEQ ID NO: 2 with a detection probe oligonucleotide.

9. The method of claim 8, wherein said detection probe oligonucleotide comprises a reporter molecule.

10. The method of claim 8, wherein said detection probe oligonucleotide comprises a flap sequence.

* * * * *

UNITED STATES PATENT AND TRADEMARK OFFICE
CERTIFICATE OF CORRECTION

| | | |
|---|---|---|
| PATENT NO. | : 11,345,949 B2 | Page 1 of 1 |
| APPLICATION NO. | : 16/318580 | |
| DATED | : May 31, 2022 | |
| INVENTOR(S) | : Allawi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 417 days.

Signed and Sealed this
Eighteenth Day of February, 2025

Coke Morgan Stewart
*Acting Director of the United States Patent and Trademark Office*